US010520513B2

(12) United States Patent
Montaner Viallonga et al.

(10) Patent No.: US 10,520,513 B2
(45) Date of Patent: Dec. 31, 2019

(54) METHODS FOR DIFFERENTIATING ISCHEMIC STROKE FROM HEMORRHAGIC STROKE

(71) Applicant: Fundació Hospital Universitari Vall D'Hebron-Institut De Recerca, Barcelona (ES)

(72) Inventors: Joan Montaner Viallonga, Barcelona (ES); Victor Llombart Sebastiá, Barcelona (ES)

(73) Assignee: Fundació Hospital Universitari Vall D'Hebron-Institut De Recerca, Barcelona (ES)

( * ) Notice: Subject to any disclaimer, the term of this patent is extended or adjusted under 35 U.S.C. 154(b) by 12 days.

(21) Appl. No.: 15/533,095

(22) PCT Filed: Dec. 3, 2015

(86) PCT No.: PCT/EP2015/078576
§ 371 (c)(1),
(2) Date: Jun. 5, 2017

(87) PCT Pub. No.: WO2016/087611
PCT Pub. Date: Jun. 9, 2016

(65) Prior Publication Data
US 2017/0269104 A1 Sep. 21, 2017

(30) Foreign Application Priority Data
Dec. 3, 2014 (EP) .................................... 14382492

(51) Int. Cl.
*G01N 33/68* (2006.01)
*G01N 33/48* (2006.01)

(52) U.S. Cl.
CPC ......... *G01N 33/6893* (2013.01); *G01N 33/48* (2013.01); *G01N 2800/2871* (2013.01)

(58) Field of Classification Search
None
See application file for complete search history.

(56) References Cited

U.S. PATENT DOCUMENTS

| 2005/0176626 | A1 | 8/2005 | Goldman et al. | |
|---|---|---|---|---|
| 2005/0181386 | A1 | 8/2005 | Diamond et al. | |
| 2006/0240480 | A1* | 10/2006 | Curdt | G01N 33/6896 435/7.1 |
| 2014/0234263 | A1* | 8/2014 | Shiels | A61K 35/22 424/93.7 |
| 2015/0119269 | A1* | 4/2015 | McPherson | G01N 33/6896 506/9 |

FOREIGN PATENT DOCUMENTS

| EP | 0005074 | 10/1979 |
|---|---|---|
| EP | 1668370 | 1/2009 |
| WO | 03016910 | 2/2003 |
| WO | 05029087 | 3/2005 |
| WO | 05106038 | 11/2005 |
| WO | 10031821 | 3/2010 |
| WO | 12036892 | 3/2012 |
| WO | 14121252 | 8/2014 |
| WO | WO-2014195698 A1 * | 12/2014 ......... G01N 33/6893 |

OTHER PUBLICATIONS

Martinez-Morillo et al., "Identification of Novel Biomarkers of Brain Damage in Patients with Hemorrhagic Stroke by Integrating Bioinformatics and Mass Spectrometry-Based Proteomics", Journal of Proteome 2013, vol. 13, pp. 969-981. (Year: 2013).*
Adams, H. P., et al., "Baseline NIH stroke scale score strongly predicts outcome after stroke; A Report of the Trial of Org 10172 in Acute Stroke Treatment (TOAST)", Neurology, vol. 53, No. 1, 1999, pp. 126-131.
Altschu, S.F., et al., "Basic Local Alignment Search Tool", J. Mol. Biol, vol. 215, 1990, pp. 403-410.
Andersen, K.K., et al., "Hemorrhagic and Ischemic Strokes Compared, Stroke Severity, Mortality, and Risk Factors", Stroke, 2009, vol. 40, pp. 2068-2072.
Brott, T. and Bogousslavsky, J., "Treatment of Acute Ischemic Stroke", The New England Journal of Medicine, vol. 343, No. 10, pp. 710-722, (2000).
Foerch C., et al., "Diagnostic Accuracy of Plasma Glial Fibrillary Acidic Protein for Differentiation Intracerebral Hemorrhage and Cerebral Ischemia in Patients with Symptoms of Acute Stroke", Clinical Chemistry, vol. 58, No. 1, 2011, pp. 237-245.
Gresle, M.M., et al., "Neurofilament Proteins as Body Fluid Biomarkers of Neurodegeneration in Multiple Sclerosis", Multiple Sclerosis International, vol. 2011, 2011, pp. 1-7.
Ingelsson E. et al., "Circulating retinol-binding protein 4, cardiovascular risk factors and prevalent cardiovascular disease in elderly", Atherosclerosis, Elsevier Ireland Ltd, IE, vol. 206, No. 1, 2009, pp. 239-244.

(Continued)

Primary Examiner — Michelle F. Paguio Frising
(74) Attorney, Agent, or Firm — Gary Gershik; Cooper & Dunham LLP

(57) ABSTRACT

The invention relates to a method for differentiating ischemic stroke from hemorrhagic stroke in a patient and to a method for selecting a patient suffering stroke for a therapy with an antithrombotic agent or with an agent capable of reducing blood pressure based on the determination of the level of GFAP in a sample of said patient in combination with one or more markers selected from the group consisting of NEF3, β-synuclein, CARNS1 and RBP4, or based on determining the level of RBP4 in a sample of said patient. Furthermore, the invention relates to a kit comprising a reagent for detecting the level of a marker selected from GFAP NEF3, β-synuclein, CARNS1, RBP4 or a combination thereof and to the use of the said kit in the methods of the invention.

23 Claims, 22 Drawing Sheets

(56) References Cited

OTHER PUBLICATIONS

Jie, K.B., "Diagnostic use of blood biomarker for discerning ischemic from hemorrhagic stroke" (Available at http://www.bestbets.org/bets/bet.php?id=2251 submitted on Jul. 11, 2011).

Kavlaci, C., et al., "Value of biomarker-based diagnostic test in differential diagnosis of hemorrhagic-ischemic stroke", Bratisl Lek Listy, vol. 112, No. 7, 2011, pp. 398-401.

Llombart, V., et al., "Plasmatic retinol-binding protein 4 and glial fibrillary acidic protein as biomarkers to differentiate ischemic stroke and intracerebral hemorrhage", Journal of Neurochemistry, vol. 136, No. 2, 2016, pp. 416-424.

Mendioroz, M., et al., "Osteopontin predicts long-term functional outcome among ischemic stroke patients", J, Neurol,, vol. 258, 2011, pp. 486-493.

Montaner, J., et al., "Differentiating ischemic from hemorrhagic stroke using plasma biomarkers: The S100B/RAGE pathway☆", J. Proteomics, vol. 75, 2012, pp. 4758-4765.

Pencina, M.J., et al., "Evaluating the added predictive ability of a new marker; From area under the ROC curve to reclassification and beyond", Statist. Med. vol. 27, 2008, pp. 157-172.

Pickering J.W. and Endre, Z.H., "New metrics for Assessing Diagnostic Potential of Candidate Biomarkers", Clin J Am Soc Nephrol, vol. 7, 2012, pp. 1355-1364.

Ramirez, R., "Type 4 retinol binding protein (RBP4) in obesity", (Testis Doctoral IBSN: 978-84-692-1530-2) (Including English Abstract), (2008).

Sasaki M., et al., "Elevation of plasma retinol-binding protein 4 and reduction of plasma adiponectin in subjects with cerebral infarction", Metabolism, Clinical and Experimental, W.B. Saunders Co., Philadelphia, PA, US, vol. 59, No. 4, 2010, pp. 527-532.

Topic, E., "Differential diagnosis and prognostic markers of stroke", The Journal of the International Federation of Clinical Chemistry and Laboratory Medicine, vol. 15, No. 3, pp. 1-3, (2004).

Tsivgoulis, G., et al., "Intensive blood reduction in acute intracerebral hemorrhage: A meta-analysis", Neurology, vol. 83, 2014, pp. 1-7.

Uhlen, M., et al., "Towards a knowledge-based Human Protein Atlas" Nature Biotechnology, vol. 28, No. 12, 2010, pp. 1248-1250.

International Search Report issued by the International Searching Authority (ISA/O.E.P.M.) dated Mar. 4, 2016 in connection with International Application No. PCT/EP2015/078576.

Zhu et al. "Evaluation of serum retinol-binding protein-4 levels as a biomarker of poor short-term prognosis in ischemic stroke.", Bioscience Reports, (2018)38, BSR20180786.

Liu et al. "Retinol-Binding Protein 4 Predicts Lesion Volume (Determined by MRI) and Severity of Acute Ischemic Stroke." Neurotoxicity Research, https://doi.org/10.1007/s12640-018-9933-z, Jul. 20, 2018.

Bamford et al. "The frequency, causes and timing of death within 30 days of stroke: the Oxfordshire Community Stroke Project", Journal of Neurology, Neurosurgery, and Psychiatry, 53: 824-829, 1990.

Xian et al. "Challenges in Assessing Hospital-Level Stroke Mortality as a Quality Measure: Comparing pf Ischemic, Intracerebral Hemorrhage, and Total Stroke Mortality Rates", Stroke http://stroke.ahajournal.org., 43:1687-1690, 2012.

\* cited by examiner

A

A

B

C

D

A

B

C

D

A

B

C

METHODS FOR DIFFERENTIATING ISCHEMIC STROKE FROM HEMORRHAGIC STROKE

TECHNICAL FIELD OF INVENTION

The invention is related to the field of diagnostic, in particular to a method of differentiating ischemic stroke from hemorrhagic stroke.

BACKGROUND OF INVENTION

Stroke remains one of the most important neurological affection. It represents the second leading cause of preventable death worldwide and a major cause of productivity impairment. The two main subtypes of stroke are ischemic stroke (IS) and intracerebral hemorrhage (ICH), also called hemorrhagic stroke. Over 80-85% of all strokes are IS caused by a brain artery occlusion, whereas the remaining 15-20% are ICH that appear due to an arterial rupture. Patients who suffer ICH presents a poorer outcome with a mortality after 30 days from symptoms onset of 37-38%, in contrast with IS patients who have a 30-days mortality of only 8-12%.

An accurate differentiation of both subtypes is critical during acute phase to prescribe the most suitable treatment protocol, which is specific and widely different between IS and ICH. The primary therapy recommended for acute IS is thrombolysis with recombinant tissue plasminogen activator (r-tPA), a serine protease that lysates the clot that occludes the brain artery. Thrombolysis has a narrow therapeutic time window of only 4.5 h from symptoms onset, thus a rapid identification of IS might allow an early recanalization leading to a recovery of the tissue from the penumbra and therefore improving the clinical outcome. On the contrary, patients with acute ICH can be managed by reducing blood pressure in order to delay hematoma growth or to avoid edema appearance and rebleedings. Some ICH patients present underlying hemostatic abnormalities that can be due to oral anticoagulant (OACs) intake, to an acquired or congenital coagulation factor deficiency or to an abnormal platelet number or functionality. In all these cases homeostasis needs to be re-established by correcting the dose of OACs or replacing the absent coagulation factor or platelets.

Nowadays stroke subtype diagnosis is mainly based on brain imaging data by computerized tomography (CT) or magnetic resonance imaging (MRI). Unfortunately, in spite of being highly sensitive, MRI and CT scans are rarely available, cannot be used repeatedly in primary hospital due to the lack of resources and may be subject to error or uncertainty if the medical personnel conducting and/or interpreting the scan are inexperienced or inadequately trained.

Several documents describe the use of biomarkers in order to carry out a rapid differentiation of stroke subtypes, such as WO2012036892 which discloses the determination of proteins such as apolipoprotein A-I preprotein, apolipoprotein A-II preprotein, apolipoprotein A-IV preprotein, apolipoprotein B precursor, apolipoprotein C-I precursor, apolipoprotein C-II precursor, apolipoprotein C-III precursor, apolipoprotein D precursor, apolipoprotein E precursor and apolipoprotein H precursor.

Kavalci C. et al (Bratisl. Lek.Listy 3011; 112) discloses using the combination of plasma biomarkers such as BNP, D-dimer, MMP9 and S100b for differential diagnosis of ischemic or hemorrhagic stroke.

Dr. K. E. Jiehas described a summary of differential diagnostic tests for stroke subtypes, highlighting the weaknesses of the studies (www.bestbets.org/bets/bet.php?id=2251).

Thus, there is a need in the art of alternative rapid biomarker-based test to overcome the limitations of the methods disclosed in the art and that they can speed-up the process of stroke subtype diagnosis and shortening the acute treatment initiation.

SUMMARY OF THE INVENTION

In one aspect, the invention relates to an in vitro method for differentiating ischemic stroke from hemorrhagic stroke in a patient, comprising
  a) determining the level of GFAP in a sample of said patient in combination with the level of one or more markers selected from the group consisting of NEF3, β-synuclein, CARNS1 and RBP4 and
  b) comparing said levels with a corresponding reference value
wherein a level of GFAP in said sample lower than the corresponding reference value and a level of NEF3, β-synuclein, CARNS1 and/or RBP4 higher than the corresponding reference value is indicative that the patient suffers ischemic stroke or wherein a level of GFAP in said sample higher than the reference value and a level of NEF3, β-synuclein, CARNS1 and/or RBP4 lower than the corresponding reference value is indicative that the patient suffers hemorrhagic stroke.

In another aspect, the invention relates to an in vitro method for selecting a patient suffering stroke for a therapy with an antithrombotic agent or with an agent capable of reducing blood pressure comprising
  a) determining the level of GFAP in a sample of said patient in combination with the level of one or more markers selected from the group consisting of NEF3, β-synuclein, CARNS1 and RBP4 and
  b) comparing said levels with a corresponding reference value
wherein a level of GFAP in said sample lower than the corresponding reference value and a level of NEF3, β-synuclein, CARNS1 and/or RBP4 higher than the corresponding reference value is indicative that the patient is a candidate for a therapy with a thrombolytic agent or
wherein a level of GFAP in said sample higher than the reference value and a level of NEF3, β-synuclein, CARNS1 and/or RBP4 lower than the corresponding reference value is indicative that the patient is a candidate for a therapy with an agent capable of reducing blood pressure.

In another aspect, the invention relates to an in vitro method for differentiating ischemic stroke from hemorrhagic stroke in a patient, comprising
  a) determining the level of RBP4 in a sample of said patient and
  b) comparing said level with a reference value
wherein a level of RBP4 in said sample higher than the reference value is indicative that the patient suffers ischemic stroke or wherein a level of RBP4 in said sample lower than the reference value is indicative that the patient suffers hemorrhagic stroke.

In another aspect, the invention relates to an in vitro method for selecting a patient suffering stroke for a therapy with an antithrombotic agent comprising
  a) determining the level of RBP4 in a sample of said patient and
  b) comparing said level with a reference value wherein a level of RBP4 in said sample higher than the reference value is indicative that the patient is a candidate for a therapy with an antithrombotic agent or wherein a level of RBP4 in said sample lower than the reference value is indicative that the patient is a candidate for a therapy with an agent capable of reducing blood pressure.

In another aspect, the invention relates to a kit comprising a reagent for detecting the level of a marker selected from GFAP, NEF3, β-synuclein, CARNS1, RBP4, or a combination thereof.

In another aspect, the invention relates to the use of the kit of the invention for differentiating ischemic stroke from hemorrhagic stroke or for selecting a patient suffering stroke for a therapy with an antithrombotic agent or with an agent capable of reducing blood pressure.

BRIEF DESCRIPTION OF THE FIGURES

The following figures are included to further show certain aspects of the present invention.

DETAILED DESCRIPTION OF THE INVENTION

Figure 1:
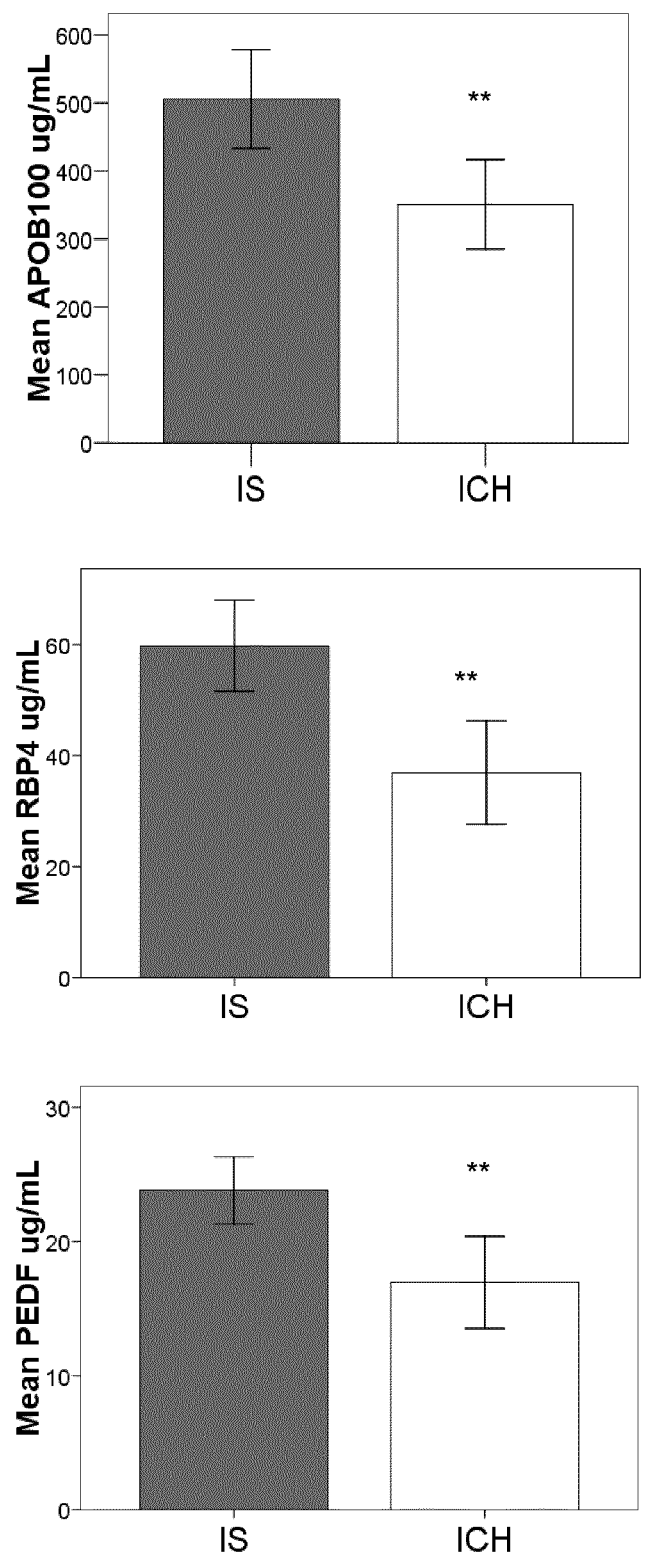
FIG. 1: Potential biomarker candidates to differentiate IS from ICH from discovery phase. * $p<0.01$; ** $p \leq 0.005$.
Figure 1:
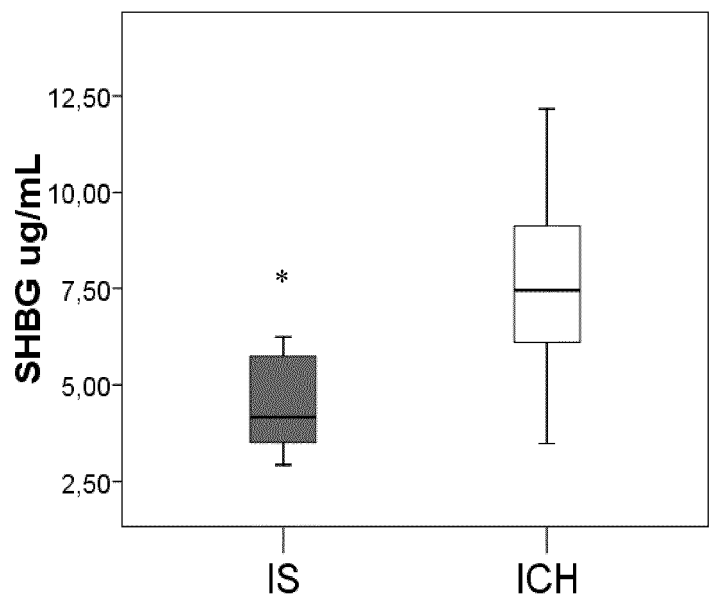
Figure 1:
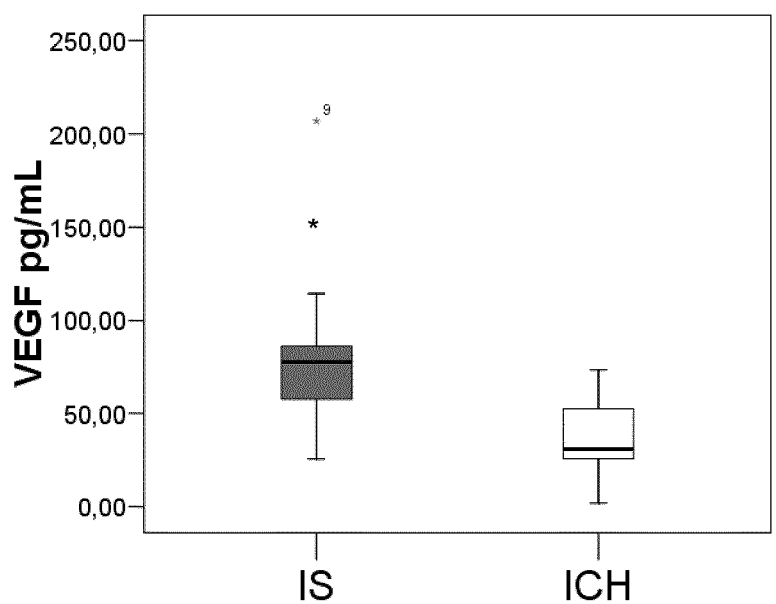

The authors of the present invention have identified RBP4 as a new plasma biomarker to differentiate acute IS and ICH (see Example 1). Additionally, GFAP in combination with one or more markers selected form the group consisting of NEF3, β-synuclein, CARNS1 and RBP4 are useful for differentiating IS and ICH (Examples 2 and 3)

Methods of the Invention

In a first aspect, the invention relates to an in vitro method for differentiating ischemic stroke from hemorrhagic stroke in a patient (first method of the invention), comprising
a) determining the level of RBP4 in a sample of said patient and
b) comparing said level with a reference value wherein a level of RBP4 in said sample higher than the reference value is indicative that the patient suffers ischemic stroke or wherein a level of RBP4 in said sample lower than the reference value is indicative that the patient suffers hemorrhagic stroke.

The term "patient", as used herein, refers to any subject which show one or more signs or symptoms typically associated with stroke such as sudden-onset face weakness, arm drift, abnormal speech as well as combination thereof such as the FAST (face, arm, speech, and time), hemiplegia and muscle weakness of the face, numbness, reduction in sensory or vibratory sensation, initial flaccidity (hypotonicity), replaced by spasticity (hypertonicity), hyperreflexia, obligatory synergies and, in particular, when they appear in one side of the body (unilateral), altered smell, taste, hearing, or vision (total or partial), drooping of eyelid (ptosis) and weakness of ocular muscles, decreased reflexes (e.g. gag, swallow, pupil reactivity to light), decreased sensation and muscle weakness of the face, balance problems and nystagmus, altered breathing and heart rate, weakness in sternocleidomastoid muscle with inability to turn head to one side, weakness in tongue (inability to protrude and/or move from side to side), aphasia, dysarthria, apraxia, visual field defect, memory deficits, hemineglect, disorganized thinking, confusion, hypersexual gestures, lack of insight of his or her, usually stroke-related, disability, altered walking gait, altered movement coordination, vertigo, headache and or disequilibrium.

The term "differentiating", as used herein, relates to the determination of a different condition. As will be understood by those skilled in the art, differentiation, although preferred to be, need not be correct for 100% of the subjects to be diagnosed or evaluated. The term, however, requires that a statistically significant portion of subjects can be identified as having an increased probability of having one of the two types of stroke. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

The term "ischemic stroke" refers to the physical blockage of blood flow to an area of the brain, causing brain cells in the area to die. Ischemic strokes can further be divided into thrombotic and embolic strokes. Thrombotic strokes occur when a brain artery is blocked by a blood clot formed in the brain. Embolic strokes are caused by a thrombus, which is formed in a peripheral artery or in the heart that travels to the brain where it produces ischemia.

The term "hemorrhagic stroke", as used herein refers to a bleeding into the brain tissue due to a blood vessel burst.

Moreover, since the biomarker identified in the present invention allows differentiating ischemic stroke from hemorrhagic stroke in a patient and considering that different therapies are applied to these two types of patients (antithrombotic agents in patients suffering ischemic stroke and an agent capable of reducing blood pressure in patients suffering hemorrhagic stroke) (see Tsivgoulis G. et al., Neurology. 2014 Sep. 19), the invention also provides method for the selection of a therapy for a patient having suffered stroke. Accordingly, in a second aspect, the invention relates to an in vitro method for selecting a patient suffering stroke for a therapy with an antithrombotic agent or for therapy with an agent capable of reducing blood pressure (second method of the invention) comprising
   a) determining the level of RBP4 in a sample of said patient and
   b) comparing said level with a reference value
wherein a level of RBP4 in said sample higher than the reference value is indicative that the patient is a candidate for a therapy with an antithrombotic agent or wherein a level of RBP4 in said sample lower than the reference value is indicative that the patient is a candidate for a therapy with an agent capable of reducing blood pressure.

The term "selecting a patient for a therapy", as used herein, relates to the identification of a patient for a therapy designed to cure a disease or palliate the symptoms associated with one or more diseases or conditions. In the particular case of a stroke therapy, it is understood any therapy which abolishes, retards or reduces the symptoms associated with stroke and, more in particular, with ischemic stroke or alternatively with hemorrhagic stroke.

As will be understood by those skilled in the art, the selection of a patient, although preferred to be, need not be adequate for 100% of the subjects selected according to the second method of the invention. The term, however, requires that a statistically significant portion of subjects were correctly selected. Whether the selection of a patient in a population of subjects is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.01, 0.05, 0.005, 0.001 or lower.

The term "antithrombotic agent", as used herein, refers to a drug that is able to reduce clot formation. Suitable antithrombotic agents for use in the present invention include, without limitation, thrombolytic agents, antiplatelet agents and anticoagulant compounds.

The term "thrombolytic agent" as used herein refers to a drug that is able to dissolve a clot. All thrombolytic agents are serine proteases and convert plasminogen to plasmin which breaks down the fibrinogen and fibrin and dissolves the clot. Currently available thrombolytic agents include reteplase (r-PA or Retavase), alteplase (t-PA or Activase), urokinase (Abbokinase), prourokinase, anisoylated purified streptokinase activator complex (APSAC), staphylokinase (Sak), atenecteplase (TNKasa), anistreplase (Eminase), streptoquinase (Kabikinase, Streptase) or uroquinase (Abokinase).

The term anticoagulant compounds, as used herein, refers to compounds that prevent coagulation and include, without limitation, vitamin K antagonists (warfarin, acenocumarol, fenprocoumon and fenidione), heparin and heparin derivatives such as low molecular weight heparins, factor Xa inhibitors such as synthetic pentasaccharides, direct thrombin inhibitors (argatroban, lepirudin, bivalirudin and ximelagatran) and antiplatelet compounds that act by inhibition of platelet aggregation and, therefore, thrombus formation and include, without limitation, cyclooxygenase inhibitors (aspirin), adenosine diphosphate receptor inhibitors (clopidrogrel and ticlopidine), phosphodiesterase inhibitors (cilostazol), glycoprotein IIB/IIIA inhibitors (Abciximab, Eptifibatide, Tirofiban and Defibrotide) and adenosine uptake inhibitors (dipiridamol).

In a preferred embodiment, the antithrombotic agent is a thrombolytic agent. In a more preferred embodiment, the thrombolytic agent is a plaminogen activator. In a yet more preferred embodiment, the plasminogen activator is tPA (tissue plasminogen activator).

The term "tissue plasminogen activator (t-PA)" as used herein refers to a serine protease found on endothelial cells that catalyzes the conversion of plasminogen to plasmin. The complete protein sequence for human t-PA has the UniProt accession number P00750 (Jul. 11, 2012). tPA may be manufactured using recombinant biotechnology techniques, tPA created this way may be referred to as recombinant tissue plasminogen activator (rtPA). Recombinant tissue plasminogen activators (r-tPAs) include alteplase, reteplase, and tenecteplase (TNKase).

Doses of t-PA should be given within the first 3 hours of the onset of symptoms or up to 4.5 hours from symptom onset. Recommended total dose: 0.9 mg/kg (maximum dose should not exceed 90 mg) infused over 60 minutes. Load with 0.09 mg/kg (10% of the 0.9 mg/kg dose) as an intravenous bolus over 1 minute, followed by 0.81 mg/kg (90% of the 0.9 mg/kg dose) as a continuous infusion over 60 minutes. Heparin should not be started for 24 hours or more after starting alteplase for stroke. Said t-PA is given intravenously and in some cases may be given directly into an artery and should be given right away after the first symptoms of stroke start.

"Blood pressure" is herein to be understood as to refer to the blood pressure at the site of central arteries, such as the aorta and carotid artery. Central blood pressure can suitably be measured non-invasively (as set out below) at the carotids or radialis by applanation tonometry. "Blood pressure" as used herein thus encompasses aortic blood pressure.

"Agent capable of reducing blood pressure", as used in the present invention, relates to any drug which lower blood pressure by different means. Among the most widely agents are the thiazide diuretics [such as furosemide, nitroprusside, hydralazine]; the ACE inhibitors, the calcium channel blockers [such as nicardipine or nimodipine]; the adrenergic receptor antagonist [such as alpha-adrenergic antagonist, urapidil], or combined alpha- and beta-blocker [labetalol and nitroglycerin]; and the angiotensin II receptor antagonists (ARBs). Illustrative, non-limitative example of agents capable of lowering or reducing blood pressure are α-methyl dopa (Aldomet), 11,17α-dimethoxy-18β-[(3,4,5-trimethoxy-benzoyl)oxyl)]-3β,2α-yohimban-16β-carboxylic acid methyl ester (Reserpine) or 2-(2,6-dichlorophenylamino) 2-imidazoline hydrochloride (Clonidine hydrochloride), lergotrile or viz. 2-chloro-6-methylergoline- 8β-acetonitrile as disclosed in EP0005074. Treatment modalities for blood pressure lowering are aimed to achieve systolic blood pressure under 180 mm Hg. In a preferred embodiment, the blood pressure may be reduced by intravenous administration of an agent capable of reducing blood pressure and co-administration of oral antihypertensive agent(s).

Any method suitable for measure arterial pressure can be used for determining if an agent is capable of reducing blood pressure, wherein a reduction in arterial pressure is detected after administration of the agent. Illustrative, non-limitative examples of methods for measurement arterial pressure are non-invasive techniques, such as by way of illustrative non-limitative example palpitation, auscultatory, oscillometric and continuous noninvasive arterial pressure (CNAP).

The term "patient", as used herein, refers to all animals classified as mammals and includes, but is not restricted to, domestic and farm animals, primates and humans, e.g., human beings, non-human primates, cows, horses, pigs, sheep, goats, dogs, cats, or rodents. Preferably, the patient is a male or female human of any age or race. Preferably the patient suffers stroke.

The first step of the methods of the invention comprises determining the level of RBP4 in a sample of said patient.

The term "sample" as used herein, relates to any sample which can be obtained from the patient. The present method can be applied to any type of biological sample from a patient, such as a biopsy sample, tissue, cell or biofluid (plasma, serum, saliva, semen, sputum, cerebral spinal fluid (CSF), tears, mucus, sweat, milk, brain extracts and the like).

In a preferred embodiment the sample is a biofluid. Illustrative non limitative biofluids are blood, plasma, serum, saliva, urine or cerebrospinal fluid. In a more preferred embodiment, the biofluid is plasma or serum.

In a preferred embodiment of the methods of the invention, the sample is obtained at baseline.

Different samples could be used for determining the level of different markers. Thus, it is not necessary that the levels of all the markers according to the methods of the invention are measured in the same type of sample. Thus, in another preferred embodiment, the levels of GFAP, CARNS1, β-synuclein and/or NEF3 are measured in serum. In another preferred the level of GFAP or RBP4, are measured in plasma.

"Baseline", as used in the present invention, is considered any time from onset of symptoms until the patient is explored for the first time. This is usually within the first hours after stroke, and it is usually the first attention in the ambulance or in the hospital. In a preferred embodiment, the baseline is within the first 4.5 hours from symptom onset, or less than 6 hours after stroke or in another preferred embodiment less than 24 hours symptoms onset.

The term "RBP4" as used herein refers to retinol binding protein 4, plasma that belongs to the lipocalin family and is the specific carrier for retinol in the blood. The complete sequence for human retinol binding protein 4 has the UniProt accession number P02753 (Aug. 8, 2013).

In a preferred embodiment, the methods of the invention further comprise determining the level of GFAP wherein reduced level of GFAP in said sample with respect to a reference value for GFAP is indicative that the patient suffers ischemic stroke or that the patient is a candidate for a therapy with a thrombolytic agent and increased level of GFAP in said sample with respect to a reference value is indicative that the patient suffers hemorrhagic stroke or that the patient is a candidate for a therapy with an agent capable of reducing blood pressure".

The term "GFAP" as used herein refers to glial fibrillary acidic protein, an intermediate filament protein that is expressed by numerous cell types of the central nervous system. The complete sequence for glial fibrillary acidic protein has the UniProt accession number P14136 (Aug. 8, 2013).

As the person skilled in the art understands, the expression levels of RBP4 and/or GFAP can be determined by measuring the levels of mRNA encoded by the corresponding genes or by measuring the levels of proteins encoded by said genes, and the levels of variants thereof.

By way of a non-limiting illustration, the expression levels are determined by means of the quantification of the levels of mRNA encoded by said genes. The latter can be quantified by means of using conventional methods, for example, methods comprising the amplification of mRNA and the quantification of the amplification product of said mRNA, such as electrophoresis and staining, or alternatively, by means of Northern blot and the use of suitable probes, Northern blot and use of specific probes of the mRNA of the genes of interest or of their corresponding cDNA/cRNA, mapping with the S1 nuclease, RT-PCR, hybridization, microarrays, etc. Similarly, the levels of cDNA/cRNA corresponding to said mRNA encoded by the marker genes can also be quantified by means of using conventional techniques; in this event, the method of the invention includes a step of synthesis of the corresponding cDNA by means of reverse transcription (RT) of the corresponding mRNA followed by the synthesis (RNA polymerase) and amplification of the cRNA complementary to said cDNA. Conventional methods of quantifying the expression levels can be found, for example, in Sambrook et al., 2001 "Molecular cloning: to Laboratory Manual", $3^{rd}$ ed., Cold Spring Harbor Laboratory Press, N.Y., Vol. 1-3.

In order to normalize the values of mRNA expression among the different samples, it is possible to compare the expression levels of the mRNA of interest in the test samples with the expression of a control RNA. A "control RNA" as used herein, relates to RNA whose expression levels do not change or change only in limited amounts. Preferably, the control RNA is mRNA derived from housekeeping genes and which code for proteins which are constitutively expressed and carry out essential cellular functions. Preferred housekeeping genes for use in the present invention include 18-S ribosomal protein, β-2-microglobulin, ubiquitin, cyclophilin, GAPDH, PSMB4, tubulin and β-actin.

Alternatively, it is also possible to determine the expression levels of the marker genes by means of the determination of the expression levels of the proteins encoded by said genes, since if the expression of genes is increased, an increase of the amount of corresponding protein should occur and if the expression of genes is decreased, a decrease of the amount of corresponding protein should occur.

The determination of the expression levels of the proteins can be carried out by immunological techniques such as ELISA, Western Blot or immunofluorescence. Western blot is based on the detection of proteins previously resolved by gel electrophoreses under denaturing conditions and immobilized on a membrane, generally nitrocellulose by the incubation with an antibody specific and a developing system (e.g. chemoluminiscent). The analysis by immunofluorescence requires the use of an antibody specific for the target protein for the analysis of the expression. ELISA is based on the use of antigens or antibodies labelled with enzymes so that the conjugates formed between the target antigen and the labelled antibody results in the formation of enzymatically-active complexes. Since one of the components (the antigen or the labelled antibody) are immobilised on a support, the antibody-antigen complexes are immobilised on the support and thus, it can be detected by the addition of a substrate which is converted by the enzyme to a product which is detectable by, e.g. spectrophotometry, fluorometry, mass spectrometry or tandem mass tags (TMT).

On the other hand, the determination of the protein expression levels can be carried out by constructing a tissue microarray (TMA) containing the subject samples assembled, and determining the expression levels of the proteins by techniques well known in the state of the art.

In a preferred embodiment the determination of the levels of the markers are determined by immunological technique. In a more preferred embodiment, the immunological technique is ELISA.

When an immunological method is used, any antibody or reagent known to bind with high affinity to the target proteins can be used for detecting the amount of target proteins. It is preferred nevertheless the use of antibody, for example polyclonal sera, hybridoma supernatants or monoclonal antibodies, antibody fragments, Fv, Fab, Fab' y F(ab')2, ScFv, diabodies, triabodies, tetrabodies and humanised antibodies.

As previously cited, the expression levels of the RBP4 and/or GFAP can be determined by measuring both the levels of protein, and the levels of variants thereof, such as fragments, isoforms, analogues and/or derivatives.

The term "functionally equivalent variant" is understood to mean all those proteins derived from RBP4 and/or GFAP sequence by modification, insertion and/or deletion or one or more amino acids, whenever the function of said variants are substantially maintained. Preferably, variants of RBP4 and/or GFAP are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (v) polypeptides resulting from RBP4 or GFAP fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

As known in the art the "similarity" between two proteins is determined by comparing the amino acid sequence and its conserved amino acid substitutes of one protein to a sequence of a second protein. The variants are defined to include polypeptide sequences different from the original sequence, preferably different from the original sequence in less than 40% of residues per segment concerned, more preferably different from the original sequence in less than 25% of residues per segment concerned, more preferably different from the original sequence in less than 10% of residues per segment concerned, more preferably different from the original sequence in only a few residues per segment concerned and, at the same time, sufficiently homologous to the original sequence to preserve functionality of the original sequence. Variants according to the present invention includes amino acid sequences that are at least 60%, 65%, 70%, 72%, 74%, 76%, 78%, 80%, 90%, or 95% similar or identical to the original amino acid sequence. The degree of identity between two proteins is determined using computer algorithms and methods that are widely known for the persons skilled in the art. The identity between two amino acid sequences is preferably determined by using the BLASTP algorithm [BLASTManual, Altschul, S., et al., NCBI NLM NIH Bethesda, Md. 20894, Altschul, S., et al., J. Mol. Biol. 215: 403-410 (1990)].

The proteins can be post-translationally modified. For example, post-translational modifications that fall within the scope of the present invention include signal peptide cleavage, glycosylation, acetylation, isoprenylation, proteolysis myristoylation, protein folding and proteolytic processing, etc. Additionally, the proteins may include unnatural amino acids fainted by post-translational modification or by introducing unnatural amino acids during translation.

The second step of the methods of the invention comprise comparing the level of RBP4 with a reference value or in the case GFAP is further determining, the method also comprises comparing the level of GFAP with a reference value.

The term "reference value", as used herein, relates to a predetermined criteria used as a reference for evaluating the values or data obtained from the samples collected from a subject. The reference value or reference level can be an absolute value; a relative value; a value that has an upper or a lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested.

According to the first method of the invention, a level of RBP4 in the sample from the patient higher than the reference value is indicative that the patient suffers ischemic stroke.

According to the second method of the invention, a level of RBP4 in said sample higher than the reference value is indicative that the patient is a candidate for a therapy with an antithrombotic agent According to the second method of the invention, a level of RBP4 in said sample lower than the reference value is indicative that the patient is a candidate for a therapy with an agent capable of reducing blood pressure.

According to the first method of the invention, reduced level of GFAP in said sample with respect to a reference value is indicative that the patient suffers ischemic stroke.

According to the second method of the invention reduced level of GFAP in said sample with respect to a reference value for GFAP is indicative that the patient is a candidate for a therapy with a thrombolytic agent.

According to the second method of the invention increased level of GFAP in said sample with respect to a reference value for GFAP is indicative that the patient is a candidate for a therapy with an agent capable of reducing blood pressure.

The levels of a biomarker are considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more higher than the reference value.

Likewise, in the context of the present invention, the level of a biomarker is reduced when the level of said biomarker in a sample is lower than a reference value. The levels of a biomarker are considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more lower than the reference value.

In a preferred embodiment the reference value for RBP4 is 49.53 µg protein/ml.

In another preferred embodiment, the reference value for GFAP is 0.07 ng protein/ml.

In another embodiment the methods of the invention further comprise determining one or more clinical parameters. Thus, the methods according to the invention may comprise determining the level of RBP4 and one or more clinical parameters or determining the levels of RBP4 and of GFAP and one or more clinical parameters The term "clinical parameters" or clinical data, as used herein, refers to person demographics (age or date of birth, race and/or ethnicity), patient clinical symptoms or signs related to stroke related diseases/conditions.

In a preferred embodiment, the clinical data is hypertension.

The term "hypertension" sometimes called arterial hypertension, as used herein refers to a chronic medical condition in which the blood pressure in the arteries is elevated. Normal blood pressure at rest is within the range of 100-140 mmHg systolic (top reading) and 60-90 mmHg diastolic (bottom reading). High blood pressure is said to be present if it is persistently at or above 140/90 mmHg.

In another preferred embodiment the clinical parameter is selected from age, NIHSS score, sex, systolic blood pressure and combinations thereof.

The term "NIHSS score", as used in the present invention refers to The National Institutes of Health Stroke Scale (NIHSS) score, a systematic assessment tool that provides a quantitative measure of stroke-related neurologic deficit (Adams H P Jr Neurology. 1999 Jul. 13; 53(1):126-31). The NIHSS was originally designed as a research tool to measure baseline data on patients in acute stroke clinical trials. Now, the scale is also widely used as a clinical assessment tool to evaluate acuity of stroke patients, determine appropriate treatment, and predict patient outcome. The NIHSS is a 15-item neurologic examination stroke scale used to evaluate the effect of acute cerebral infarction on the levels of consciousness, language, neglect, visual-field loss, extraocular movement, motor strength, ataxia, dysarthria, and sensory loss. A trained observer rates the patient's ability to answer questions and perform activities. Ratings for each item are scored with 3 to 5 grades with 0 as normal, and there is an allowance for untestable items. The level of stroke severity as measured by the NIH stroke scale scoring system: 0=no stroke, 1-4=minor stroke, 5-15=moderate stroke, 15-20=moderate/severe stroke, 21-42=severe stroke. In the present invention the term "higher score" refers to a score from 5 to 42 in the NIH stroke scale scoring system.

In another aspect, the invention relates to an in vitro method for differentiating ischemic stroke from hemorrhagic stroke in a patient (third method of the invention), comprising
  a) determining the level of GFAP in a sample of said patient in combination with the level of one or more markers selected from the group consisting of NEF3, β-synuclein, CARNS1 and RBP4 and
  b) comparing said levels with a corresponding reference value
wherein a level of GFAP in said sample lower than the corresponding reference value and a level of NEF3, β-synuclein, CARNS1 and/or RBP4 higher than the corresponding reference value is indicative that the patient suffers ischemic stroke or wherein a level of GFAP in said sample higher than the reference value and a level of NEF3, β-synuclein, CARNS1 and/or RBP4 lower than the corresponding reference value is indicative that the patient suffers hemorrhagic stroke.

"NEF3", NFM or NEFM, as used herein relates to the neurofilament medium polypeptide involved in the maintenance of neuronal caliber. The complete sequence for human NEF3 has the UniProt accession number P07197 (Nov. 11, 2015)

"β-synuclein", as used herein relates to a protein that Protects neurons from staurosporine and 6-hydroxy dopamine (6OHDA)-stimulated caspase activation in a p53/TP53-dependent manner. The complete sequence for human β-synuclein has the Uniprot accession number Q16143 ((Nov. 11, 2015)

"CARNS1", also kwon as ATP-grasp domain-containing protein 1 and as used herein relates to carnosine synthase 1, an enzyme that catalyzes the synthesis of carnosine and homocarnosine. The complete sequence for human CARNS1 has the Uniprot accession number A5YM72 (Nov. 11, 2015).

In another aspect, the invention relates to an in vitro method for selecting a patient suffering stroke for a therapy with an antithrombotic agent or with an agent capable of reducing blood pressure (fourth method of the invention) comprising
  a) determining the level of GFAP in a sample of said patient in combination with the level of one or more markers selected from the group consisting of NEF3, β-synuclein, CARNS1 and RBP4 and
  b) comparing said levels with a corresponding reference value
wherein a level of GFAP in said sample lower than the corresponding reference value and a level of NEF3, β-synuclein, CARNS1 and/or RBP4 higher than the corresponding reference value indicative that the patient is a candidate for a therapy with a thrombolytic agent or wherein a level of GFAP in said sample higher than the reference value and a level of NEF3, β-synuclein, CARNS1 and/or RBP4 lower than the corresponding reference value is indicative that the patient is a candidate for a therapy with an agent capable of reducing blood pressure.

In a preferred embodiment the third or the fourth method of the invention, the method comprises determining the level of GFAP and one marker selected from the group consisting of NEF3, β-synuclein, CARNS1 and RBP4. Thus in a preferred embodiment, the third or fourth method of the invention comprises determining GFAP and NEF3; GFAP and β-synuclein; GFAP and CARNS1; or GFAP and RBP4.

In another preferred embodiment, the third or the fourth method of the invention comprises determining the level of GFAP and two markers selected from the group consisting of NEF3, β-synuclein, CARNS1 and RBP4. Thus, in a preferred embodiment the third or fourth method of the invention comprises determining GFAP, NEF3 and β-synuclein; GFAP, NEF3 and CARNS1; GFAP, NEF3 and RBP4; GFAP, β-synuclein and CARNS1; GFAP, β-synuclein and RBP4; or GFAP, CARNS1 and RBP4.

In another preferred embodiment, the third or the fourth method of the invention comprises determining the level of GFAP and three markers selected from the group consisting of NEF3, β-synuclein, CARNS1 and RBP4. Thus, in a preferred embodiment the third or fourth method of the invention comprises determining GFAP, NEF3, β-synuclein and CARNS1; GFAP, NEF3, β-synuclein and RBP4; GFAP, NEF3, CARNS1 and RBP4; or GFAP, β-synuclein, CARNS1 and RBP4.

In another preferred embodiment, the third or the fourth method of the invention comprises determining the level of GFAP and four markers NEF3, β-synuclein, CARNS1 and RBP4. Thus in a preferred embodiment, the third and fourth method of the invention comprises determining GFAP, NEF3, β-synuclein, CARNS1 and RBP4.

In a more preferred embodiment the third and fourth method of the invention comprises determining the level of level of GFAP and NEF3; GFAP and β-synuclein; GFAP, NEF3 and β-synuclein; GFAP and CARNS1; GFAP, CARNS1 and NEF3; GFAP, CARNS1 and RBP4; GFAP, β-synuclein and RBP4, GFAP, NEF and RBP4 or GFAP and RBP4.

All the terms and embodiments previously described in relation to the first and second methods of the invention are equally applicable to the third and fourth method of the invention.

Kit of the Invention

In another aspect, the invention relates to a kit comprising a reagent for detecting the level of a marker selected from GFAP, NEF3, β-synuclein, CARNS1, RBP4, or a combination thereof.

The term "kit", as used herein, refers to a product containing the different reagents necessary for carrying out the methods of the invention packed so as to allow their transport and storage. Materials suitable for packing the components of the kit include crystal, plastic (e.g. polyethylene, polypropylene, polycarbonate), bottles, vials, paper, or envelopes.

Additionally, the kits of the invention can contain instructions for the simultaneous, sequential or separate use of the different components which are in the kit. Said instructions can be in the form of printed material or in the form of an electronic support capable of storing instructions susceptible of being read or understood, such as, for example, electronic storage media (e.g. magnetic disks, tapes), or optical media (e.g. CD-ROM, DVD), or audio materials. Additionally or alternatively, the media can contain internet addresses that provide said instructions.

The reagents of the kit include compounds that bind specifically to the marker proteins. Preferably, said compounds are antibodies, aptamers or fragments thereof.

In a preferred embodiment, the reagent is an antibody or fragments thereof.

The antibodies of the kit of the invention can be used according to techniques known in art for determining the protein expression levels, such as, for example, flow cytometry, Western blot, ELISA, RIA, competitive EIA, DAS-ELISA, techniques based on the use of biochips, protein microarrays, or assays of colloidal precipitation in reactive strips.

The antibodies can be fixed to a solid support such as a membrane, a plastic or a glass, optionally treated to facilitate the fixation of said antibodies to the support. Said solid support comprises, at least, a set of antibodies which specifically recognize the marker, and which can be used for detecting the levels of expression of said marker.

Additionally, the kits of the invention comprise reagents for detecting a protein encoded by a constitutive gene. The availability of said additional reagents allows normalizing the measurements performed in different samples (for example, the sample to be analyzed and the control sample) to rule out that the differences in the expression of the biomarkers are due to a different quantity of total protein amount in the sample more than the real differences in the relative levels of expression. The constitutive genes in the present invention are genes that are always active or being transcribed constantly and which encode for proteins that are expressed constitutively and carry out essential cellular functions. Proteins that are expressed constitutively and can be used in the present invention include, without limitation, β-2-microglobulin (B2M), ubiquitin, 18-S ribosomal protein, cyclophilin, GAPDH, PSMB4, tubulin and actin In a preferred embodiment, the reagents for assaying the levels of the different biomarkers comprise at least 10%, at least 20%, at least 30%, at least 40%, at least 50%, at least 60%, at least 70%, at least 80%, at least 90% or at least 100% of the total amount of reagents for assaying biomarkers forming the kit. Thus, in the particular case of kits comprising reagents for assaying the levels of RBP4 and/or GFPA, the reagents specific for said biomarkers (i.e. antibodies which bind specifically to RBP4 and/or GFPA) comprise at least 10%, at least 20%, at least 30%, at least 40%, at least 50%, at least 60%, at least 70%, at least 80%, at least 90% or at least 100% of the antibodies present in the kit.

In another aspect, the invention relates to the use of the kit of the invention for differentiating ischemic stroke from hemorrhagic stroke or for selecting a patient suffering stroke for a therapy with an antithrombotic agent or with an agent capable of reducing blood pressure.

In a preferred embodiment, the invention relates to the use of the kit of the inventions in the first, second, third or fourth method of the invention.

In another preferred embodiment, the kit of the invention comprises a reagent for determining the level of GFAP and a reagent for determining the level of one marker selected from the group consisting of NEF3, β-synuclein, CARNS1 and RBP4. Thus in a preferred embodiment, the kit of the invention comprises reagents for determining the level of GFAP and NEF3; GFAP and β-synuclein; GFAP and CARNS1; or GFAP and RBP4.

In another preferred embodiment, the kit of the invention comprises a reagent for determining the level of GFAP and reagents for determining the level of two markers selected from the group consisting of NEF3, β-synuclein, CARNS1 and RBP4. Thus, in a preferred embodiment the kit of the invention comprises reagents for determining the levels of GFAP, NEF3 and β-synuclein; GFAP, NEF3 and CARNS1; GFAP, NEF3 and RBP4; GFAP, β-synuclein and CARNS1; GFAP, β-synuclein and RBP4; or GFAP, CARNS1 and RBP4.

In another preferred embodiment, the kit of the invention comprises a reagent for determining the level of GFAP and reagents for determining the level of three markers selected from the group consisting of NEF3, β-synuclein, CARNS1 and RBP4. Thus, in a preferred embodiment the kit of the invention comprises reagent for determining the level of GFAP, NEF3, β-synuclein and CARNS1; GFAP, NEF3, β-synuclein and RBP4; GFAP, NEF3, CARNS1 and RBP4; or GFAP, β-synuclein, CARNS1 and RBP4.

In another preferred embodiment, the kit of the invention comprises a reagent for determining the level of GFAP and reagents for determining the levels of four markers NEF3, β-synuclein, CARNS1 and RBP4. Thus in a preferred embodiment, the kit of the invention comprises reagents for determining the level of GFAP, NEF3, β-synuclein, CARNS1 and RBP4.

In a more preferred embodiment the kit of the invention comprises reagents for determining the level of GFAP and NEF3; GFAP and β-synuclein; GFAP, NEF3 and β-synuclein; GFAP and CARNS1; GFAP, CARNS1 and NEF3; GFAP, CARNS1 and RBP4; GFAP, β-synuclein and RBP4, GFAP, NEF and RBP4 or GFAP and RBP4.

All the terms and embodiments previously described in relation to the methods of the invention are equally applicable to the kit of the invention.

The invention will be described by way of the following examples which are to be considered as merely illustrative and not limitative of the scope of the invention.

EXAMPLES

Materials and Methods
Study Population

A total number of 170 acute stroke patients admitted to the emergency department of Vall d'Hebrón University Hospital (Barcelona, Spain) from 2004 to 2010 were included (example 1). A total number of 74 stroke patients were admitted to the emergency department of Vall d'Hebrón University Hospital (Barcelona, Spain) from 2012 to 2015 were included (examples 2 and 3). Stroke diagnosis was based on a standardized and previously described protocol of clinical and neuroradiological assessment (Mendioroz, M. et al. Osteopontin predicts long-term functional outcome among ischemic stroke patients. *J. Neurol.* 258, 486-493 (2011). Stroke severity was assessed by using the National Institutes of Health Stroke Scale (NIHSS) (Brott, T. & Bogousslaysky, J. Treatment of acute ischemic stroke. *N. Engl. J. Med.* 343, 710-722 (2000)). Plasma was immediately separated in EDTA tubes by centrifugation at 1500 g for 15 min at 4° C. and stored at −80° C. until use and clinical data was collected blinded to plasma biomarkers results (Montaner, J. et al. Differentiating ischemic from hemorrhagic stroke using plasma biomarkers: the S100B/RAGE pathway. *J. Proteomics* 75, 4758-4765 (2012)). Written consent was obtained from all patients in accordance with Helsinki declaration.

Discovery Phase

Example 1

A total number of 9 plasma pools were obtained from individual samples of 36 ischemic stroke (IS) patients matched by age, sex, NIHSS and stroke etiology. Each pool was formed by 4 individual samples from patients with similar clinical characteristics that were mixed by agitation during 2 hours at 4° C. These 9 pools were compared with individual plasma samples obtained from 10 patients with intracerebral hemorrages (ICH).

A library of 177 human proteins was screened with multiplexed sandwich-ELISAs from SearchLight® platform (AushonBioSystems, Billerica, Mass., USA), based on chemiluminiscent detection of molecules whose respective capture-antibodies were combined in 96-well plates.

Examples 2 and 3

A first selection of candidate protein biomarkers was based on the Human Protein Atlas (HPA) version 13 (Uhlen, M. et al. Towards a knowledge-based Human Protein Atlas. Nat. Biotechnol. 2010, 28 (12), 1248-50.). HPA provides the expression profiles for proteins in 48 different human tissues and in more than 40 cell types. The data of protein expression are based on immunohistochemistry results obtained on tissue micro arrays. The complete list of all proteins included in the Human Protein Atlas was downloaded from http://www.proteinatlas.org/about/download and those proteins with supportive information were selected ("supportive" means that more than one antibody reported similar patterns of expression of the protein). Proteins with supportive data were sorted using to criteria: i) proteins with a high/medium expression in brain tissues (cerebral cortex, lateral ventricles, hippocampus and cerebellum) and low or undetected in other tissues; ii) proteins with a high expression in glial cells and undetected in other cell types. The first criteria was used to obtain a list of brain enriched proteins, whereas the second criteria was used to obtain a list of proteins specific from glial cells, similar to the expression profile of the protein GFAP.

A second list of protein candidates was composed by the proteins of the neurofilament family. This family of proteins are the major structural proteins of neurons and show a high abundance in larger neurons, axons and long projection axons (Melissa M. et al Neurofilament Proteins as Body Fluid Biomarkers of Neurodegeneration in Multiple Sclerosis). The members of this family are neurofilament medium polypeptide (NEF3), neurofilament light polypeptide (NEFL), neurofilament heavy polypeptide (NEFH), alpha internexin (Ina), peripherin (Per) and Synemin (Syn).

First Replication Phase

Example 1

Candidate proteins were selected from the previous analysis regarding their statistical differences between ischemic and hemorrhagic stroke: Sexual Hormone Binding Globulin (SHBG) and Vascular Endothelial Growth Factor (VEGF) were analyzed by ELISA (R&D systems, USA); and Apolipoprotein B-100 (Apo B-100), Pigment Neurotrophic Derived Factor (PEDF) and Retinol Binding Protein 4 (RBP4) were analyzed by multiplexed sandwich-ELISAs from SearchLight® platform (AushonBioSystems, Billerica, Mass., USA)

These proteins were tested in individual plasma samples obtained during the first 6 hours from symptoms onset from 20 IS patients and 20 ICH matched by age and sex and with similar NIHSS. In both phases (discovery and replication) biomarkers results were blinded to clinical data. Each sample was assayed twice with a CV lower than 20% and the mean value was used for the analysis.

Examples 2 and 3

The levels of the selected candidates were analysed using the HPA approach Oligodendrocyte Myelin glycoprotein (OMG) (Cusabio, PR China), Neurogranin (NRGN) (Cusabio), Centriole, cilia and spindle-associated protein (C1orf96) (MyBiosource, USA), β-synuclein (antibodies on-line, Germany), Carnosine syntase 1 (CARNS1) (Mybiosource), Beta-1 adrenergic receptor (ADRB1) (Cusabio), Voltage-dependent P/Q-type calcium channel subunit alpha-1A (CAC1A) (Elabscience, PR China) and Juxtanodin (Mybiosource) were detected by ELISA immunoassay. A total of 74 stroke patients (40 IS and 34 ICH) were included in this analysis.

Levels of Neurofilament medium polypeptide (NEF3) (Elabsicence, PR China), Neurofilament heavy polyppeetide (NFH) (Cusabio), Neurofilament light polypeptide (NFL) (Cusabio), Alpha internexin (Ina) (LS bio, USA), Peripherin (Per) (Antibodies on-line) and synemin (Syn) (Mybiosource) were analyzed by ELISA immunoassay in a subgroup of 31 patients (15 IS and 16 ICH). Proteins from the neurofilaments family that showed significant differences among groups were analyzed in the whole cohort of 74 patients.

The levels of GFAP, Juxtanodin, CARNS1, OMG, NRGN, Beta synuclein, NEF3, NFL, Synemin, Peripherin and Alpha internexin were measured in serum. The levels of RBP4, ADRB1, CAC1A and C1orf96 were measured in plasma.

Second Replication Phase

Example 1

Proteins which remained significantly different among stroke subtypes were analyzed in individual plasma samples obtained during the first 4.5 hours from symptom onset from a second independent cohort of 38 IS patients and 28 ICH. These proteins were analyzed together with Glial Fibrillary Acidic Protein (GFAP)(AbNova, Taiwan).

Statistical Analysis

SPSS statistical package 15.0 was used for statistical analysis (example 1) and SPSS statistical package 22 as used for statistical analysis (examples 2 and 3). Intergroup differences were assessed by Pearson chi-squared test for categorical variables. Nonnality was assessed by Shapiro-Wilk test for the Discovery phase and Kolmogorov-Smirnov test for the Replication phase. For continuous variables, those normally distributed (p>0.05) were analyzed by Student's t test or ANOVA and mean and standard deviation (SD) values are given whereas for variables with non-normal distribution Mann-Whitney U or Kruskal-Wallis test were used and median and interquartile range (IQR) are reported. Receiver operator characteristics (ROC) curves were used for each biomarker in order to obtain the cut-off points with optimal accuracy (both sensitivity and specificity) to predict stroke subtype. In all cases, a p<0.05 was considered significant at a 95% confidence level. To build predictive models, the considered clinical variables were included in a forward stepwise multivariate logistic regression analysis. Afterward biomarkers alone or in combination were added by Enter method to clinical predictive models. Odds ratios (ORadj) and 95% confidence intervals (CI) were given. AUC from logistic regression models were compared by De Long method using Medcalc v12.3.

Integrated Discrimination Improvement (IDI)

It is a comparative statistical contributing additional to that provided by the Areas under the curve of the ROC curves (AUC) information. One way to quantify the difference between the probabilities determined by the predictive model between ischemic and hemorrhagic biomarkers adding stroke model is by calculating the IDI.

Calculation of the IDI is done by computing average predicted probabilities of subjects who developed the event of interest and the predicted ability of subjects who did not reach the event in models with and without the added biomarkers(s), and subtracting the values from cases and controls from each other. The increase in the difference between cases and controls after addition of the biomarkers (s) is the integrated discrimination improvement. Thus, the IDI is equivalent to the improvement in the difference between the average predicted risk of individuals who developed an event and the average predicted risk of individuals who did not develop an event Therefore, the calculation of IDI provides a numerical value to the difference between the model with and without biomarkers, while the AUC only indicates which model has greater discrimination. In addition, the IDI reveals whether the model is better at predicting events (high sensitivity) or non-events (high specificity), providing a more comprehensive idea of the discrimination model (Pencina M J et al., Stat Med 2008; 27(2): 157-172).

Using R software (Hmisc and PredictABEL packages), NRI and IDI indexes were calculated to assess the added value FMPPs to the clinical predictive models. In NRI test, pre-specified clinically relevant thresholds of predicted risk (<10% and >90%) were used to calculate reclassification of patients into risk outcome groups.

In all cases a p value <0.05 was considered statistically significant.

Net Reclassification Improvement (NRI)

The net reclassification improvement (NRI) is an increasingly popular measure for evaluating improvements in risk predictions. NRI allows knowing the change in the probability predicted by the model with biomarkers with respect to the clinical model. The NRI assesses the net number of individuals correctly reclassified by adding biomarkers to the model; eg in a model predicting long-term disability, the number of patients who actually suffer a disability are classified as events by the predictive model including biomarkers and were not in the clinical model. In the same way that the IDI, the calculation contemplates currency NRI the number of patients for both events and for non-events (Pencina M J et al., Stat Med 2008; 27(2):157-172).

The NRI can be calculated with the probabilities considered as a continuous variable, where the increase in the probability at a point indicates a change of category or categories of risk defaulting and observing individuals who change from one risk group to another. The use of categorical NRI is recommended, usually with a maximum of three risk groups (low, medium, high) and which include clinically relevant percentages as indicated by the predictive model; the use of continuous NRI or with additional categories will result in an overestimation of the reclassification rate (Pickering J W et al., Clin J Am Soc Nephrol CJASN. 2012 August; 7(8):1355-64).

Example 1—Results

Nine pooled-plasma samples from stroke patients with acute IS and 10 individual plasma samples from ICH patients were screened in a 177 protein library in the discovery phase No difference was found for age neither for sex distribution among both groups of patients. Among 177 analysed proteins only 18 were found to have different levels regarding stroke subtypes. From these 18 proteins, 14 were higher in IS and 4 were higher in ICH (p<0.1) (Table 1).

TABLE 1

Biomarker level regarding subtype of stroke. List of 18 proteins that were found at different concentration between plasma pool of IS patients and individual plasma samples from ICH patients. Those biomarkers normally distributed are expressed as mean ± SD and those non-normally distributed were described as median (IQR). Those proteins that were selected for further replications are highlighted in bold. (p < 0.05, significantly different; p < 0.1, trend). ACRP30: Adiponectin APO B-100: Apolipoprotein B-100; BMP-9: Bone Morphogenetic Protein 9; CC16: Clara Cell Protein; CD 14: Cluster of differentiation 14; EGF: Epidermal growth Factor; IGFBP 3: Insulin-like Growth Factor Binding Protein 3; MIP 1a: Macrophage Inflammatory Protein 1 alpha; PEDF: Pigment Epithelium Derived factor; RBP4: Retinol Binding Protein 4; SCF: Stem Cell Factor; SHBG: Sexual Hormone Binding globulin; TARC: Thymus and Activation-Regulated Chemokine; VCAM1: Vascular Cell Adhesion Molecule 1; VEGF: Vascular Endothelial Growth Factor.

| Protein | IS | ICH | p |
|---|---|---|---|
| Eotaxin | 72.28 ± 13.11 pg/mL | 55.34 ± 22.46 pg/mL | 0.061 |
| CD14 | 2.04 ± 0.3 µg/mL | 2.65 ± 0.7 µg/mL | 0.021 |
| PEDF | 23.82 ± 3.76 µg/mL | 16.95 ± 5.44 µg/mL | 0.006 |
| Clusterin | 39.66 ± 6.02 µg/mL | 33.92 ± 6.92 µg/mL | 0.072 |
| APO B-100 | 506.81 ± 110.03 µg/mL | 349.56 ± 104.55 µg/mL | 0.005 |
| RBP4 | 59.8 ± 12.32 µg/mL | 36.94 ± 14.68 µg/mL | 0.002 |
| SCF | 1.16 ± 0.24 ng/mL | 0.80 ± 0.38 ng/mL | 0.028 |
| IGFBP 3 | 686.18 ± 107.01 ng/mL | 518.10 ± 228.53 ng/mL | 0.096 |
| TARC | 105.3 (95.6-125.3) pg/mL | 65.25 (51.4-125.6) pg/mL | 0.072 |
| EGF | 56.4 (47.1-87.8) pg/mL | 31.95 (14-37.1) pg/mL | 0.011 |
| CC16 | 12.62 (9.76-17.33) ng/mL | 7.53 (6.41-12.73) ng/mL | 0.034 |
| MIP 1a | 5.5 (3.6-7.9) pg/mL | 1.25 (0.75-5.4) pg/mL | 0.07 |
| VCAM1 | 1.68 (1.26-2.25) µg/mL | 2.14 (1.70-4.61) µg/mL | 0.086 |
| ACRP 30 | 8.57 (7.458-11.835) µg/mL | 10.71 (9.41-22.17) µg/mL | 0.085 |
| SHBG | 4.17 (3.50-5.75) µg/mL | 7.45 (6.1-9.12) µg/mL | 0.009 |
| VEGF | 77.6 (57.7-86) pg/mL | 30.75 (25.9-52.5) pg/mL | 0.007 |
| I 309 | 1.8 (1.6-2.6) pg/mL | 0.15 (0.15-0.15) pg/mL | 0.012 |
| BMP 9 | 24.3 (20.2-29.6) pg/mL | 14.3 (12.80-17.40) pg/mL | 0.01 |

Five proteins showed the most significant difference (p<0.01). Four of them were higher in IS than ICH: Pigment Epithelium Derived Factor (PEDF) (p=0.006) Apolipoprotein B-100 (APO B-100) (p=0.005), Retinol Binding Protein 4 (RBP4) (p=0.002) and Vascular Endothelial Growth Factor (VEGF) (p=0.007). Only Sexual Hormone Binding Globulin (SHBG) was found to be higher in ICH when compared with IS (p=0.009) (FIG. 1) (Table 2).

Figure 2:
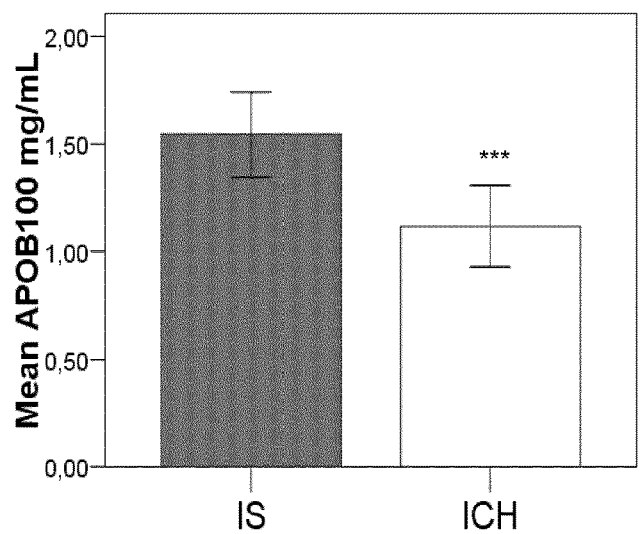
FIG. 2: Results from the first replication phase. * $p<0.05$,  $p<0.01$, * $p<0.005$.
Figure 2:
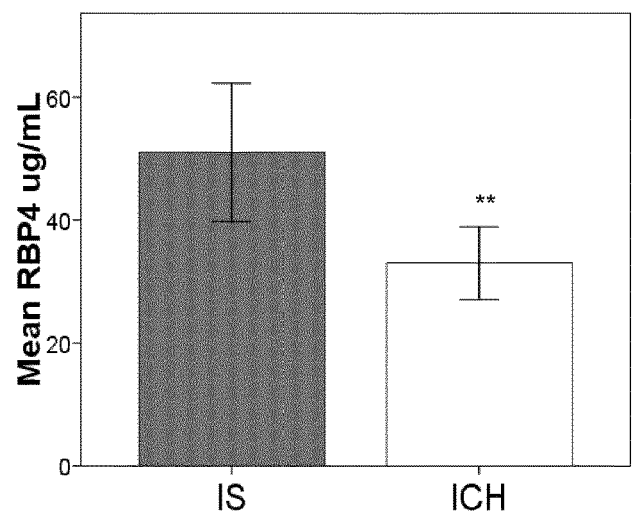
Figure 2:
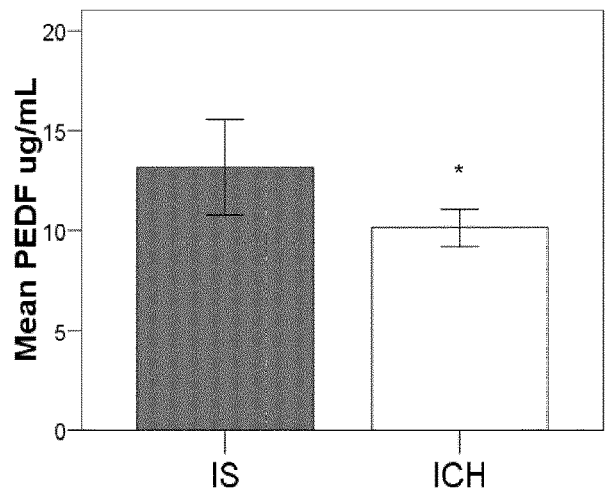
Figure 2:
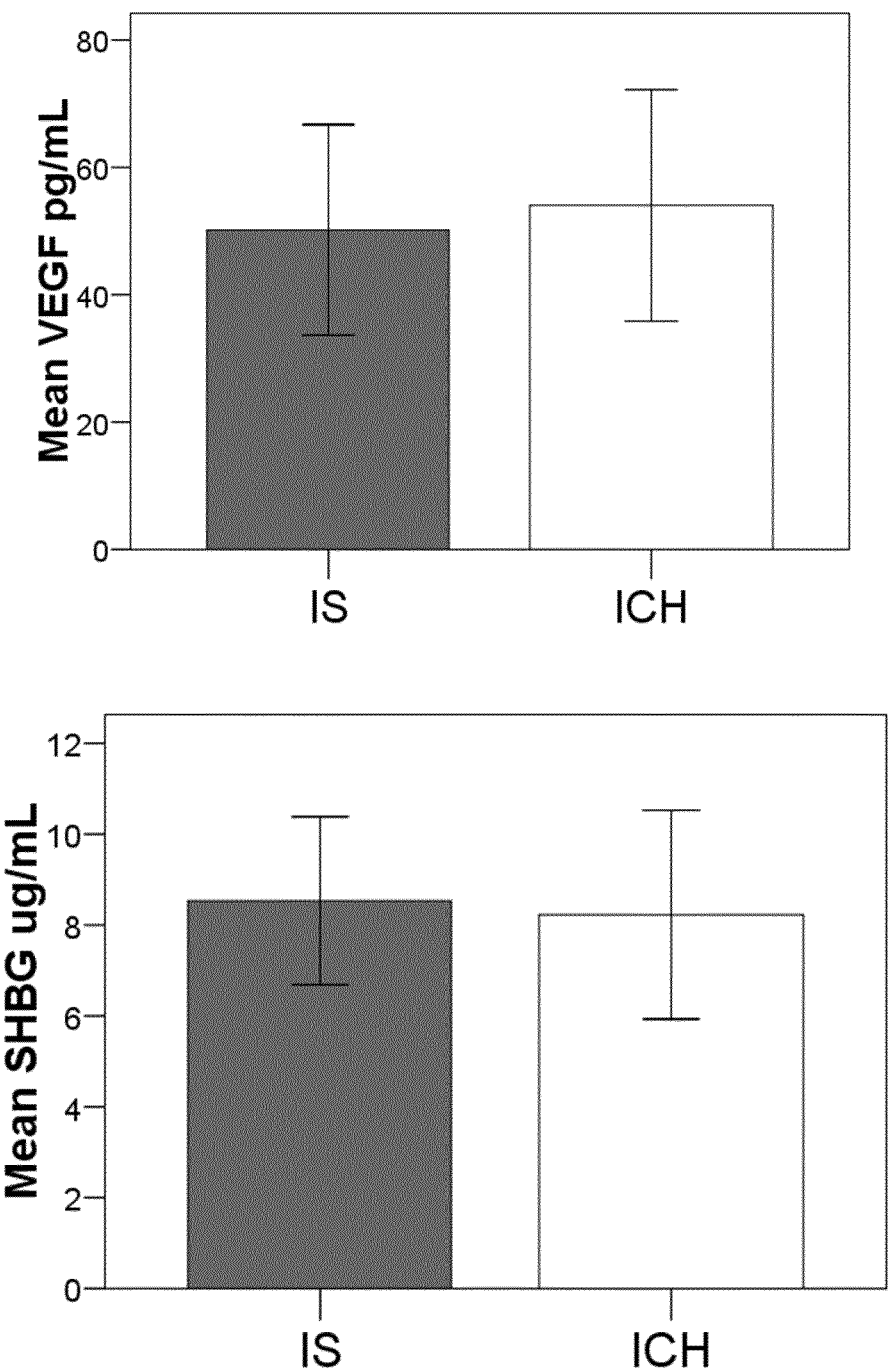

A first replication phase was conducted in an independent cohort of 20 IS and 20 ICH acute stroke patients (<6 h from symptoms onset) matched by age, sex and NIHSS. IS stroke patients had plasma higher concentrations of RBP4, APO B-100 and PEDF than patients with ICH (p=0.009; p=0.003 and p=0.028, respectively), whereas no difference was found on levels of SHBG (p=0.839) neither VEGF (p=0.756) (FIG. 2) (Table 2).

TABLE 2

Candidate biomarker levels in each experimental phase regarding stroke subtype. List of candidate biomarkers that were analyzed during each experimental stage is shown. Those biomarkers normally distributed are expressed as mean ± SD and those non-normally distributed were described as median (IQR). Ultimate candidate biomarkers selected for logistic regression analysis are highlighted in bold. (p < 0.05, significantly different; p < 0.1, trend)

| Biomarker | Stroke subtype | Mean/median | Std. deviation | p |
|---|---|---|---|---|
| Discovery Phase | | | | |
| APO B-100 | IS | 506.81 µg/mL | ±110.28 | 0.005 |
| | ICH | 349.56 µg/mL | ±104.55 | |
| PEDF | IS | 23.81 µg/mL | ±3.76 | 0.006 |
| | ICH | 16.95 µg/mL | ±5.44 | |
| RBP4 | IS | 59.81 µg/mL | ±12.32 | 0.002 |
| | ICH | 36.94 µg/mL | ±14.68 | |
| SHBG | IS | 4.17 µg/mL | 3.5-5.75 | 0.009 |
| | ICH | 7.45 µg/mL | 6.1-9.12 | |
| VEGF | IS | 77.6 pg/mL | 57.7-86 | 0.007 |
| | ICH | 30.75 pg/mL | 25.9-52.5 | |
| First Replication Phase | | | | |
| APO B-100 | IS | 1540 µg/mL | ±440 | 0.003 |
| | ICH | 1120 µg/mL | ±430 | |
| PEDF | IS | 13.17 µg/mL | ±5.4 | 0.028 |
| | ICH | 10.14 µg/mL | ±2.05 | |
| RBP4 | IS | 51.05 µg/mL | ±24.65 | 0.009 |
| | ICH | 33 µg/mL | ±12.8 | |
| SHBG | IS | 8.53 pg/mL | ±4.03 | 0.839 |
| | ICH | 8.2 pg/mL | ±5.13 | |
| VEGF | IS | 50.17 pg/mL | ±36 | 0.765 |
| | ICH | 54.02 pg/mL | ±39.64 | |
| Second Replication Phase | | | | |
| APO B-100 | IS | 820 µg/mL | ±290 | 0.285 |
| | ICH | 900 µg/mL | ±250 | |
| GFAP | IS | 0.04 ng/mL | 0.04-0.04 | <0.0001 |
| | ICH | 0.08 ng/mL | 0.04-0.68 | |
| PEDF | IS | 11.26 µg/mL | ±4.72 | 0.653 |
| | ICH | 10.65 µg/mL | ±5.9 | |
| RBP4 | IS | 56.75 µg/mL | ±21.48 | 0.011 |
| | ICH | 44.23 µg/mL | ±15.03 | |

RBP4, APOB100 and PEDF were tested in a third cohort of hyperacute stroke patients (<4.5 h of evolution from symptoms onset) with 38 IS and 28 ICH. These three candidates were analysed together with GFAP and RAGE which have been widely reported to be associated with hemorrhagic and ischemic stroke respectively. In this cohort, more IS patients suffered from hypertension (p=0.005) and ischemic cardiopathy (p=0.004) than patients with ICH. Atrial fibrillation and dyslipidemia were mildly associated with IS (p=0.111 and p=0.101, respectively) and sex male was related to ICH (p=0.107) but only close to a trend (Table 3).

TABLE 3

Baseline demographic characteristics and risk factors profile in second replication phase cohort. Those factors highlighted in bold showed statistically significant differences between IS and ICH (p < 0.05) and were included in the logistic regression analysis. However, hypertension remained as the only clinical variable independently associated with IS and considered in the clinical model.

| Variable | IS stroke patients (n = 38) | ICH patients (n = 28) | p |
|---|---|---|---|
| Sex (male) n (%) | 18 (47.4%) | 17 (68%) | 0.107 |
| Age (mean ± SD) | 72.28 ± 11.57 | 76.03 ± 10.98 | 0.2 |
| Previous stroke, n (%) | 4 (10.5%) | 0 (0%) | 0.286 |
| Hypertension, n (%) | 31 (81.6%) | 12 (48%) | 0.005 |
| Diabetes, n (%) | 12 (31.6%) | 9 (36%) | 0.716 |
| Tobacco, n (%) | 2 (5.3%) | 3 (12%) | 0.377 |
| Atrial Fibrillation | 13 (34.2%) | 4 (16%) | 0.111 |
| Ischemic Cardiopathy | 10 (26.3%) | 0 (0%) | 0.004 |
| Dyslipidemia | 11 (29.7%) | 3 (12%) | 0.101 |
| NIHSS | 14.13 ± 8.37 | 13.95 ± 6.35 | 0.925 |

Figure 3:
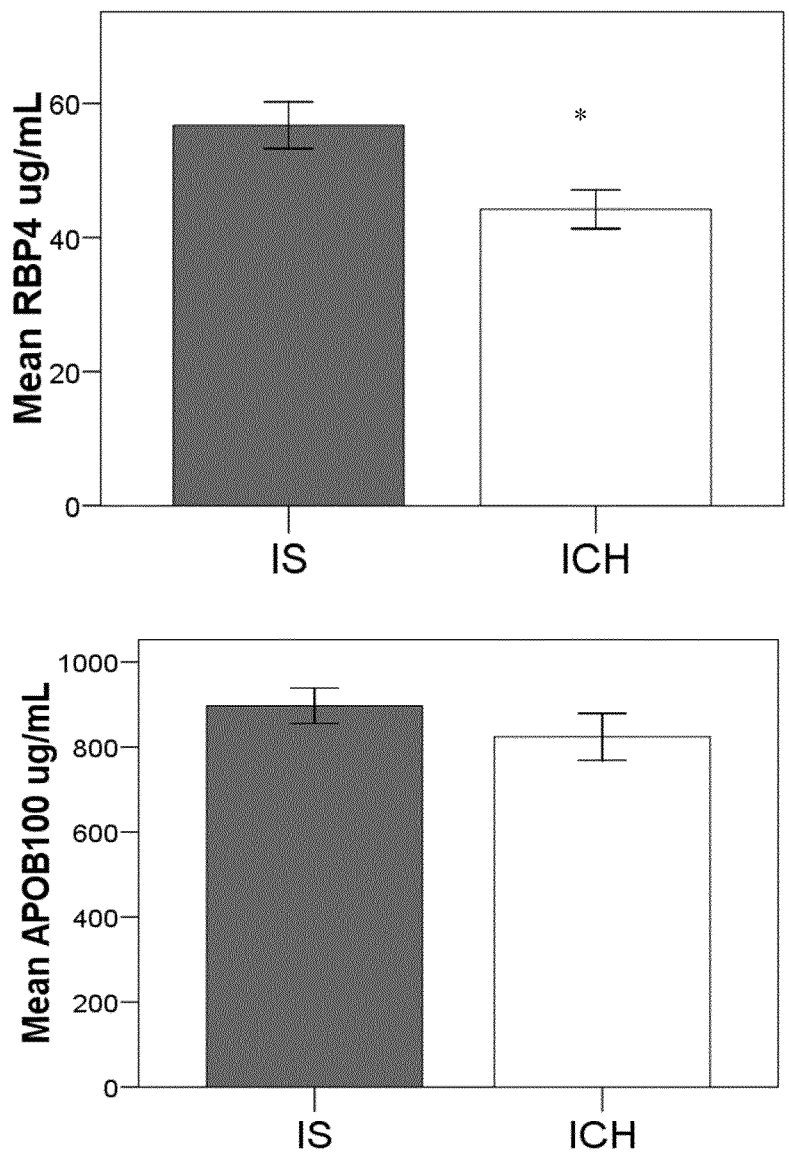
FIG. 3: Plasma levels of RBP4, APOB100, RAGE and GFAP in IS and ICH patients in the second replication phase. * $p<0.05$, ** $p<0.0001$.
Figure 3:
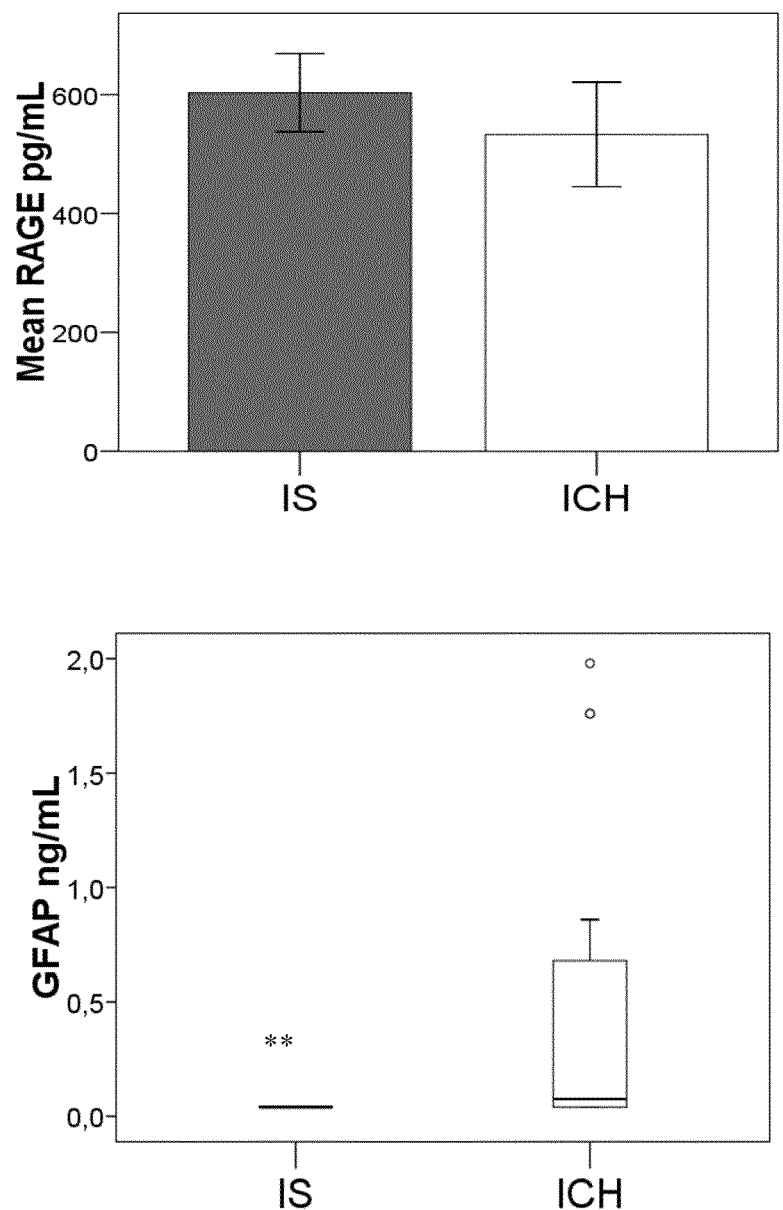

Plasma levels of RBP4 were more elevated in IS when compared to ICH (p=0.011) while GFAP was significantly higher in ICH (p<0.0001) (FIG. 3). No difference in plasma concentrations of APO B-100 and RAGE were found between both stroke subtypes (Table 2). PEDF results were excluded for further analysis because of high CV between interplate controls.

Figure 4:
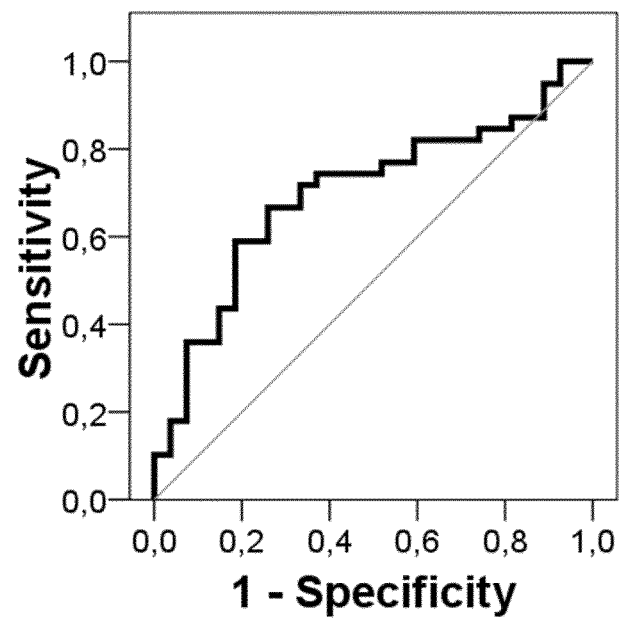
FIG. 4: A) RBP4 and GFAP ROC curves. B) Specificity and sensitivity to differentiate IS stroke from ICH for cut-off points of RBP4>49.53 μg/mL and GFAP<0.07 ng/mL.
Figure 4:
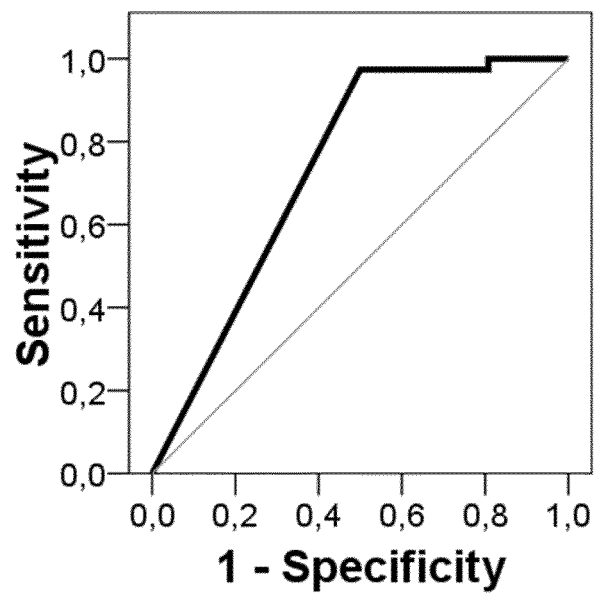
Figure 4:
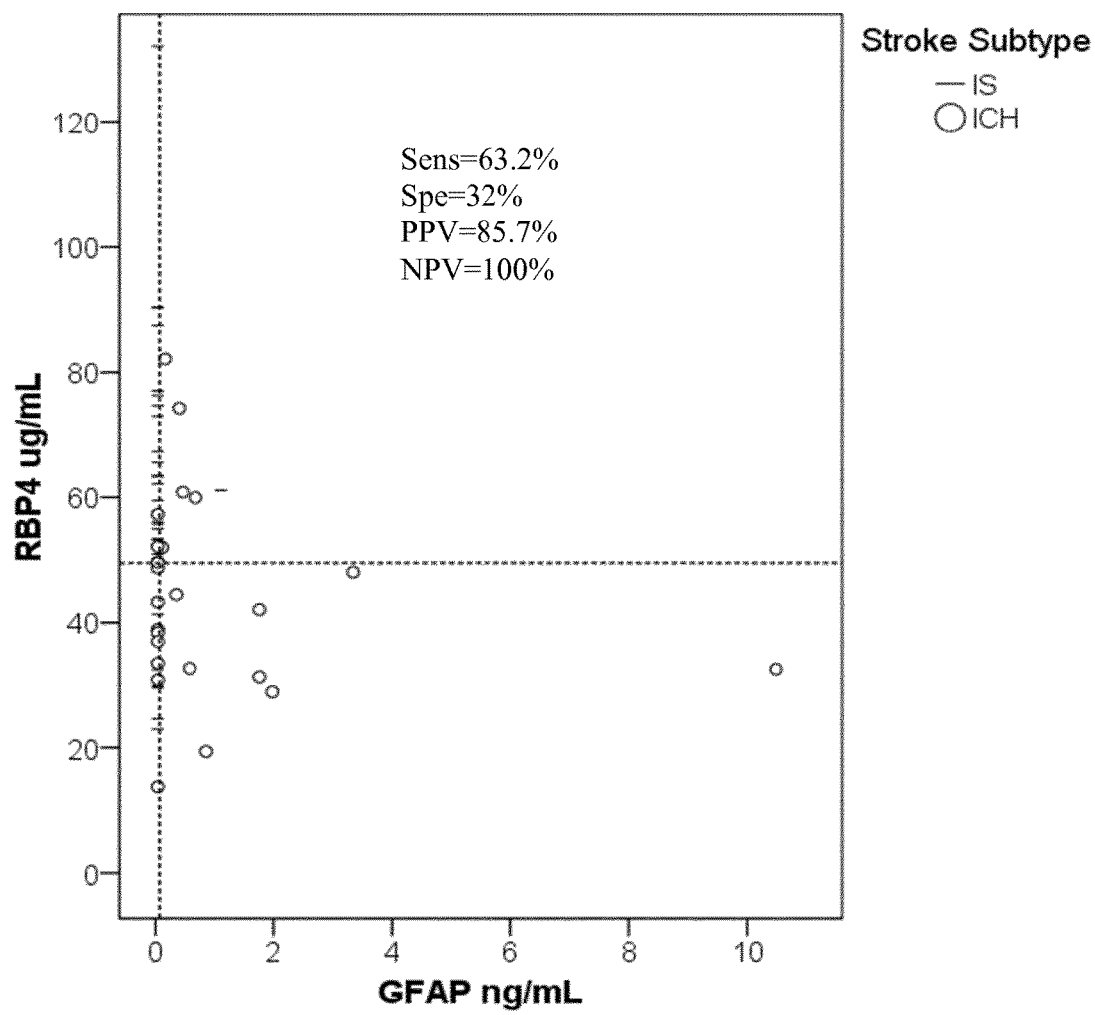

Taking into account RBP4 as the only biomarker that differentiated IS from ICH in all replication steps and GFAP, the inventors determined by ROC curve analysis RBP4>49.53 µg/mL and GFAP<0.07 ng/mL as the best biomarker cut-off points to differentiate IS from ICH (sensitivity=63.2%; specificity=32%; PPV (Positive predictive value)=85.7% and NPV (Negative predictive value)=100%) (FIG. 4).

Figure 5:
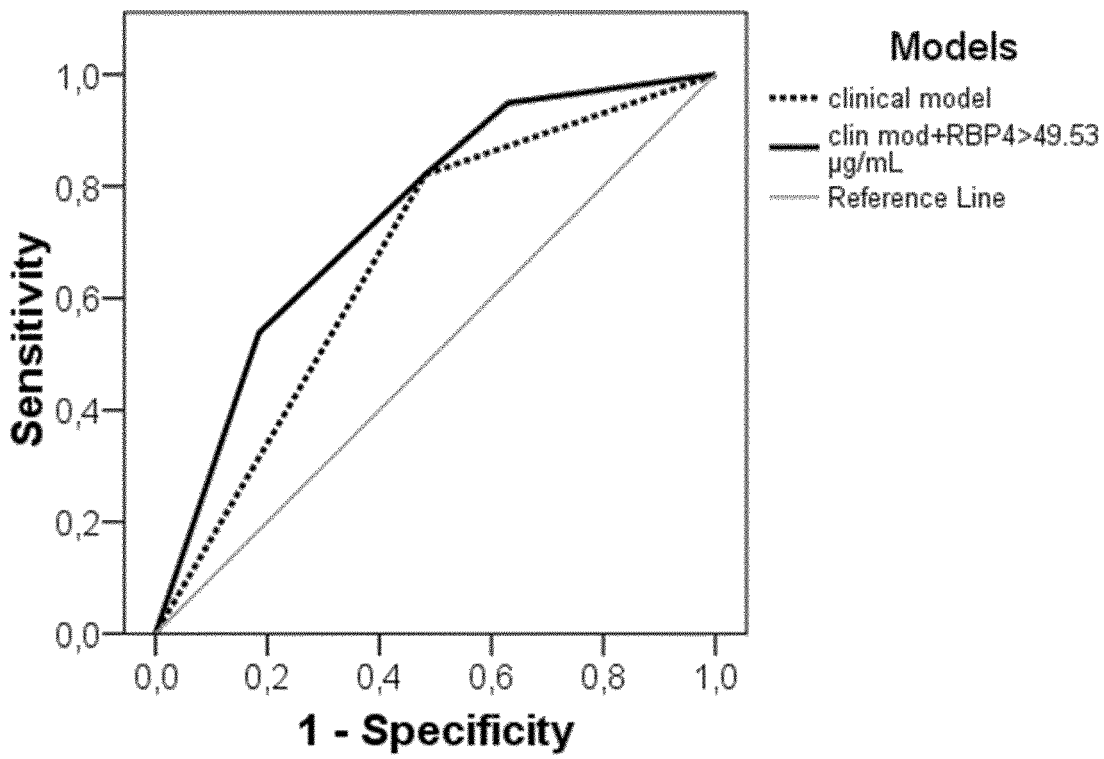
FIG. 5: ROC curves of all logistic regression models. A) Clinical model vs RBP4 model; B) clinical model vs GFAP model; C) clinical model vs RBP4 and GFAP model; D) clinical model vs combined RBP4 and GFAP model.
Figure 5:
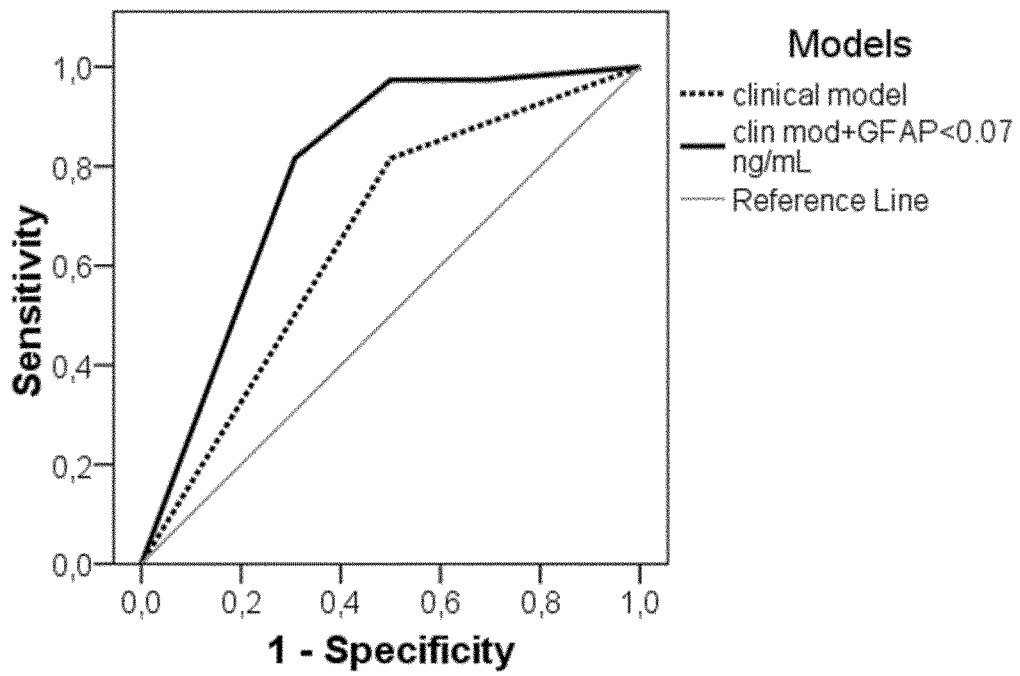
Figure 5:
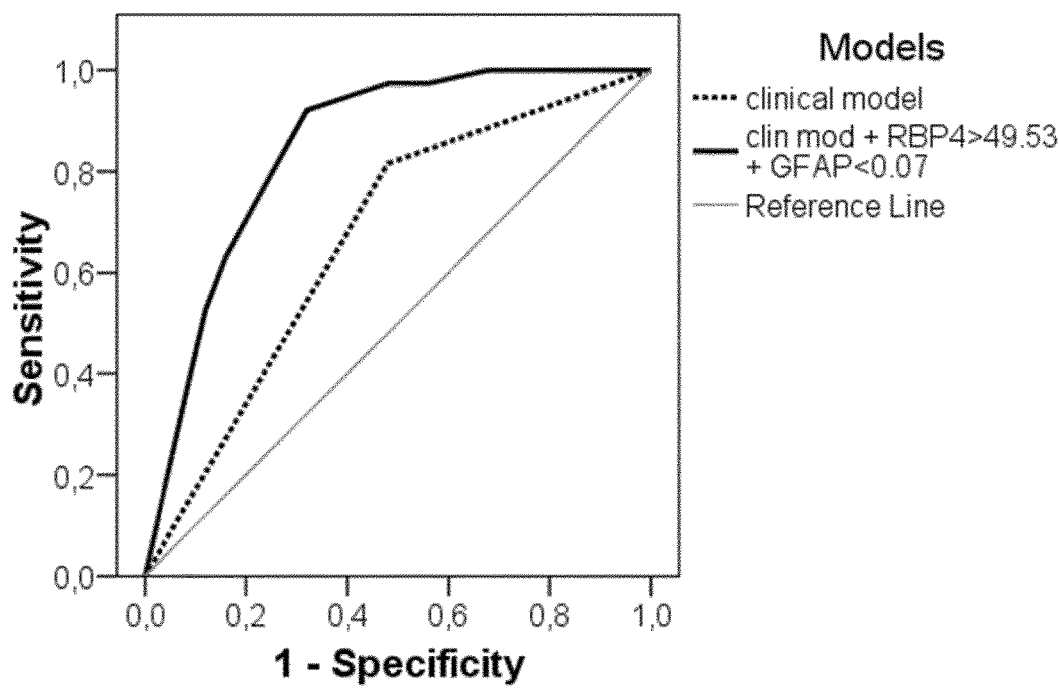
Figure 5:
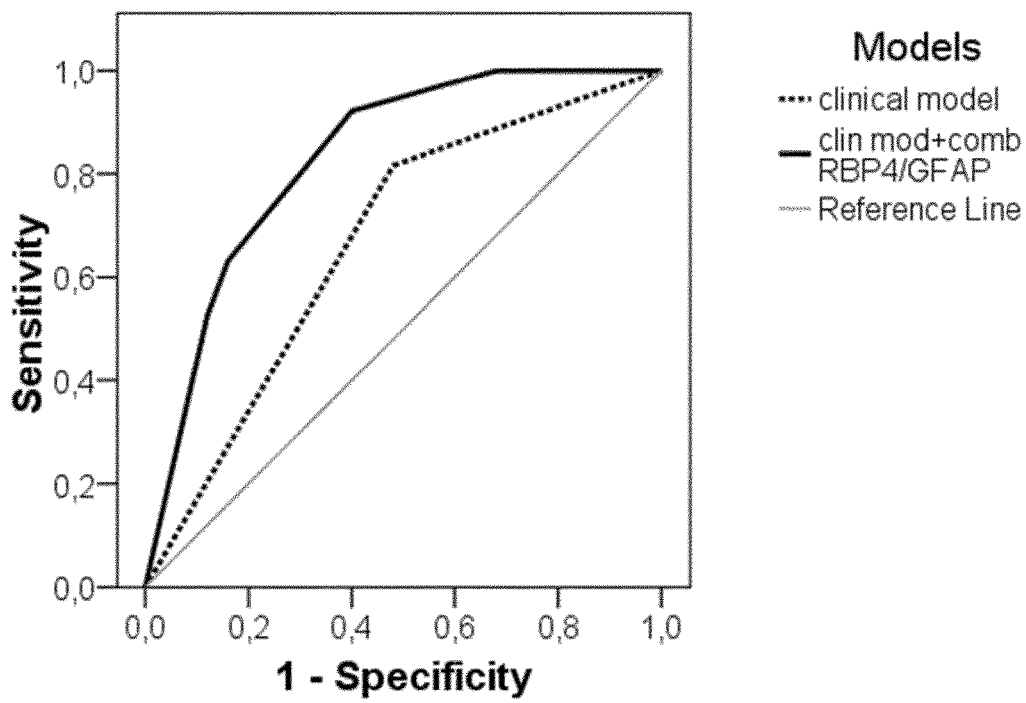

The logistic regression analysis showed hypertension as the only clinical variable independently associated with IS ($OR_{adj}$ 4.571 [95% CI 1.516-13.781] p=0.007). Both, RBP4 and GFAP dicotomized by each cut-off point were added separately (RBP4: $OR_{adj}$ 3.99 [95% CI 1.03-15.450] p=0.045; GFAP: $OR_{adj}$ 0.029 [95% CI 0.003-0.272] p=0.029) or in combination ($OR_{adj}$ 7.591 [95% CI 2.422-23.79] p=0.001) (Table 4). The AUC (area under curve) of the clinical model excluding biomarkers was 0.658 (CI 95% [0.521-0.795]). This area was increased when RBP4 (AUC=0.743 (CI 95% [0.620-0.867]), p=0.0368) or GFAP (AUC=0.788 (CI 95% [0.665-0.911]), p=0.0046) were included in the clinical model. However the model with the best discriminating ability was the one with the clinics and both RBP4 and GFAP (AUC=0.847 (CI 95% [0.740-0.953]), p=0.0028) when compared with the clinical variable alone (FIG. 5).

The authors analyzed the integrated discrimination improvement (IDI) and net reclassifications improvement (NRI) indexes to further assess the added value of RBP4 and GFAP to the clinical basis. By determining plasma concentration of both biomarkers they were able to significantly increase the discrimination between subjects who suffered an IS and those who suffered ICH (IDI index 29.3%, p=$6.6*10^{-6}$). Furthermore, the combination of RBP4 and GFAP significantly reclassified into higher risk categories (NRI index 60.63%, p=0.0002) (Table 4).

TABLE 4

Comparison between predictive models. $OR_{adj}$ (95% CI) and p-value are given for all logistic regression models. Biomarkers were added to clinical logistic regression model using cut-off point: RBP4 > 49.53 µg/mL and GFAP < 0.07 ng/mL. AUC: Area Under the ROC Curve; area with 95% CI given for each model. Clinical model always used as reference model to compare. Statistically significant are highlighted in bold.

Model Ischemic Stroke

| | | Clinical model | Clinical model + RBP4 | Clinical model + GFAP | Clinical model + RBP4 + GFAP | Clinical model + RBP4/ GFAP |
|---|---|---|---|---|---|---|
| Logistic regression (OR adj) | HTA | 4.571 [95% CI 1.516-13.781] p = 0.007 | 4.736 [95% CI 1.466-15.304] p = 0.009 | 2.412 [95% CI 0.629-9.255] p = 0.199 | 2.442 [95% CI 0.587-10.155] p = 0.219 | 3.154 [95% CI 0.829-11.991] p = 0.092 |
| | RBP4 | — | 3.845 [95% CI 1.270-11.642] p = 0.017 | — | 3.990 [95% CI 1.030-15.450] p = 0.045 | 7.591 [95% CI 2.422-23.793] p = 0.001 |
| | GFAP | — | — | 0.035 [95% CI 0.004-0.305] p = 0.002 | 0.029 [95% CI 0.003-0.272] p = 0.002 | |
| IDI statistics | IDI events | — | 0.043 | 0.103 | 0.139 | 0.117 |
| | IDI non-events | — | 0.032 | 0.131 | 0.154 | 0.121 |
| | IDI | — | 0.075 (0.006-0.144) | 0.234 (0.109-0.360) | 0.293 (0.166-0.421) | 0.238 (0.127-0.349) |
| | p-value | ref | 0.03 | 0.0002 | $6.6*10^{-6}$ | $2048*10^{-5}$ |

TABLE 4-continued

Comparison between predictive models. $OR_{adj}$ (95% CI) and p-value are given for all logistic regression models. Biomarkers were added to clinical logistic regression model using cut-off point: RBP4 > 49.53 µg/mL and GFAP < 0.07 ng/mL. AUC: Area Under the ROC Curve; area with 95% CI given for each model. Clinical model always Comparison between predictive models. $OR_{adj}$ (95% CI) and p-value are given for all logistic regression models. Biomarkers were added to clinical logistic regression model using cut-off point: RBP4 > 49.53 µg/mL and GFAP < 0.07 ng/mL. AUC: Area Under the ROC Curve; area with 95% CI given for each model. Clinical model always used as reference model to compare. Statistically significant are highlighted in bold.
Model Ischemic Stroke

|  |  | Clinical model | Clinical model + RBP4 | Clinical model + GFAP | Clinical model + RBP4 + GFAP | Clinical model + RBP4/ GFAP |
|---|---|---|---|---|---|---|
| Categorical NRI | NRI events | — | 0 | −0.026 | −0.027 | 0.526 |
|  | NRI non-events | — | 0 | 0.320 | 0.440 | 0.080 |
|  | NRI | — | 0 | 0.294 [0.066-0.5214] | 0.413 [0.1486-0.6788] | 0.6063 [0.2863-0.9263] |
|  | p-value | ref | — | 0.01146 | 0.002 | 0.0002 |
| ROC curve | AUC | 0.658 (0.521-0.795) | 0.743 (0.620-0.867) | 0.788 (0.665-0.911) | 0.847 (0.740-0.953) | 0.803 (0.721-0.939) |
|  | p-value | Ref. | 0.0368 | 0.0046 | 0.0028 | 0.0046 |

The same analysis was performed with a clinical model adjusted bay age, sex and NIHSS as previously described (Montaner, 2012 cited supra), together with HTA.

Figure 6:
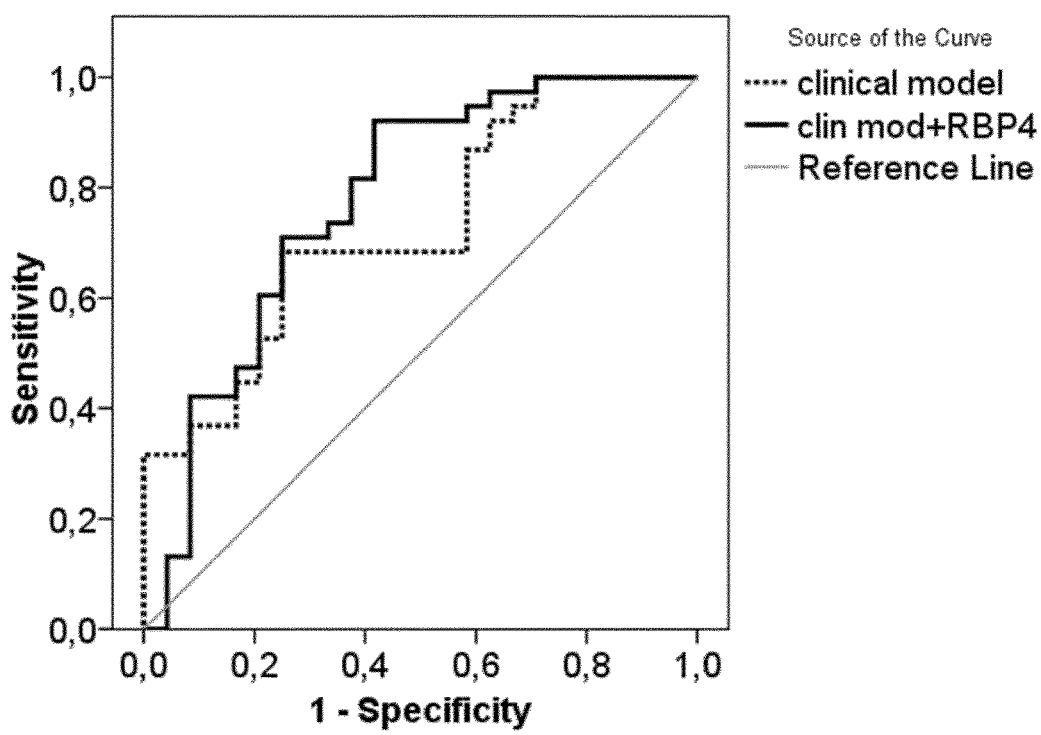
FIG. 6: ROC curves of all logistic regression models. A) Adjusted Clinical model vs clinical model and RBP4 cut-off point; B) adjusted clinical model vs GFAP cut-off point; C) adjusted clinical model vs RBP4 and GFAP cut-off point; D) adjusted clinical model vs RBP4 and GFAP cut-off points combined in a single variable.
Figure 6:
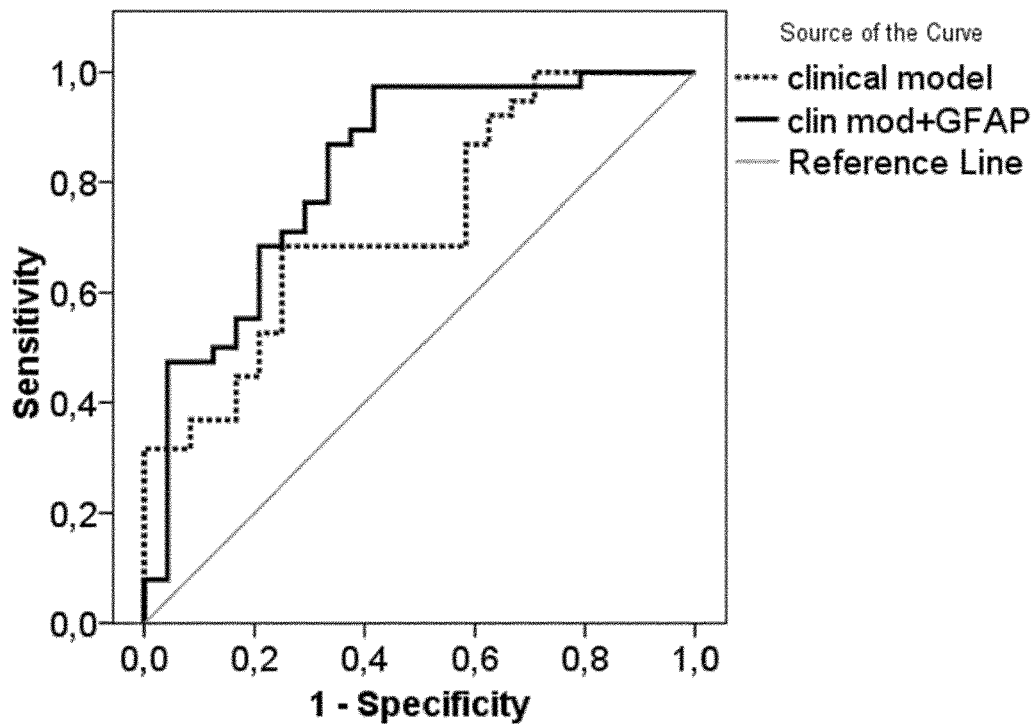
Figure 6:
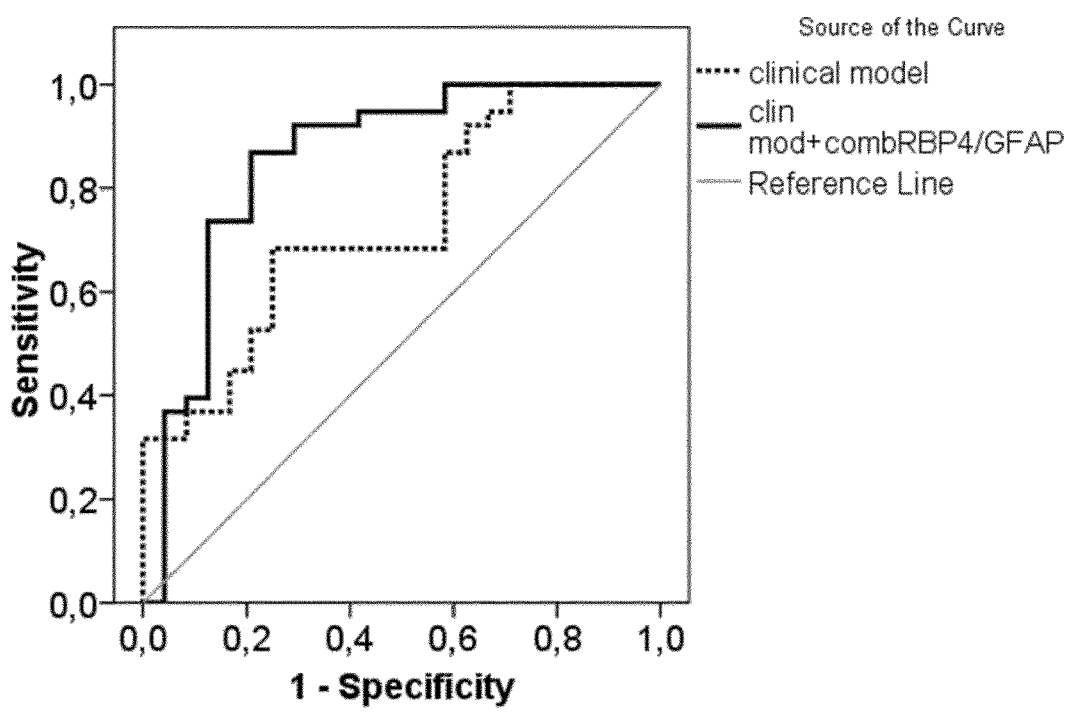
Figure 6:
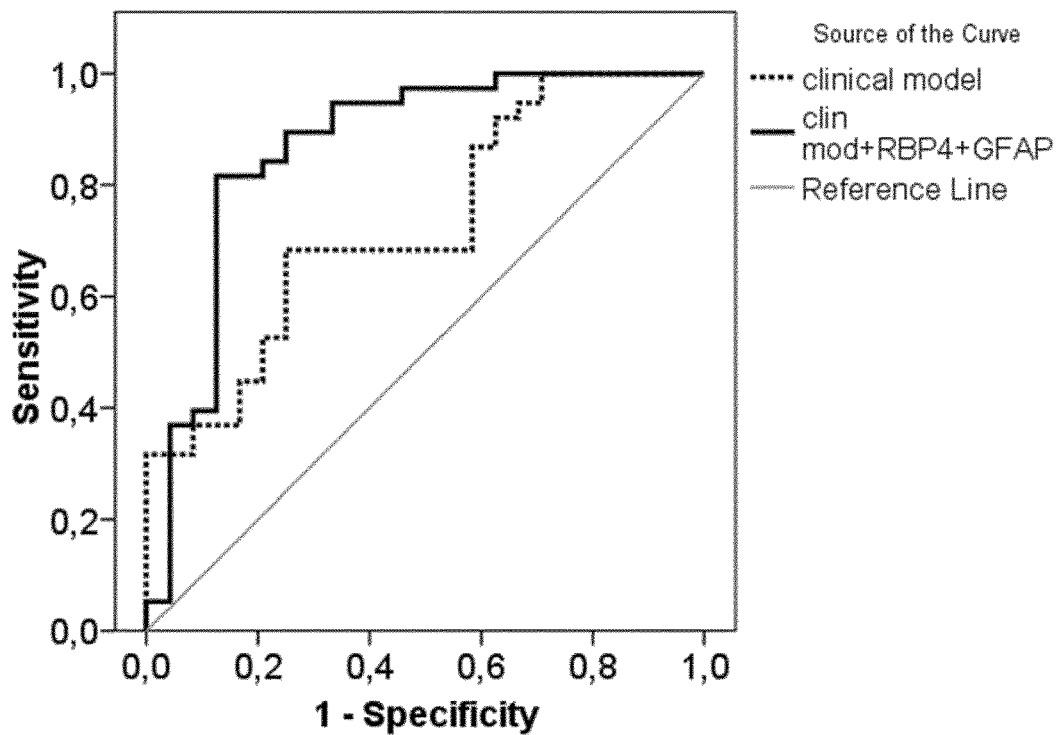

In the logistic regression analysis both, RBP4 and GFAP dicotomized by each cut-off point were added separately (RBP4: $OR_{adj}$ 4.673 [95% CI 1.331-16.404] p=0.016; GFAP: 0.034 [95% CI 0.003-0.332] p=0.004) or in combination ($OR_{adj}$ 9.423 [95% CI 2.450-36.249] p=0.001) (Table 5). The AUC of the adjusted clinical model excluding biomarkers was 0.731 (CI 95% [0.605-0.858]). This area was increased when RBP4 (AUC=0.775 (CI 95% [0.648-0.903])) or GFAP (AUC=0.823 (CI 95% [0.712-0.935]) were included in the clinical model. However the model with the best discriminating ability was the one with the clinics and both RBP4 and GFAP (AUC=0.867 (CI 95% [0.763-0.972]), p=0.04) when compared with the clinical variable alone (FIG. 6) (Table 5).

The inventors also analyzed the integrated discrimination improvement (IDI) and net reclassifications improvement (NRI) indexes to further assess the added value of RBP4 and GFAP to the clinical basis. By determining plasma concentration of both biomarkers the inventors were able to significantly increase the discrimination between subjects who suffered an IS and those who suffered ICH (IDI index 27.6%, p=$1.98*10^{-5}$). Furthermore, the combination of RBP4 and GFAP significantly reclassified into higher risk categories (NRI index 60.63%, p=$1*10^{-5}$) (Table 5).

TABLE 5

Multivariate logistic regression with an adjusted clinical model by age, sex and NIHSS.
Model Ischemic Stroke

|  |  |  | Adjusted Clinical model | Adjusted Clinical model + RBP4 | Adjusted Clinical model + GFAP | Adjusted Clinical model + RBP4 + GFAP | Adjusted Clinical model + RBP4/ GFAP |
|---|---|---|---|---|---|---|---|
| Logistic regression (OR adj) | Age |  | 1.019 [95% CI 0.969-1.071] p = 0.465 | 1.033 [95% CI 0.977-1.091] p = 0.253 | 1.015 [95% CI 0.960-1.073] p = 0.597 | 1.036 [95% CI 0.970-1.107] p = 0.296 | 1.044 [95% CI 0.978-1.114] p = 0.196 |
|  | Sex |  | 0.398 [95% CI 0.123-1.285] p = 0.124 | 0.423 [95% CI 0.121-1.482] p = 0.179 | 0.502 [95% CI 0.133-1.893] p = 0.309 | 0.568 [95% CI 0.136-2.375] p = 0.438 | 0.550 [95% CI 0.137-2.217] p = 0.401 |
|  | NIHSS |  | 1.013 [95% CI 0.937-1.095] p = 0.747 | 0.973 [95% CI 0.983-1.060] p = 0.534 | 1.043 [95% CI 0.953-1.141] p = 0.362 | 0.996 [95% CI 0.894-1.110] p = 0.996 | 0.974 [95% CI 0.881-1.077] p = 0.610 |
|  | HTA |  | 3.880 [95% CI 1.219-12.351] p = 0.022 | 4.182 [95% CI 1.209-14.465] p = 0.024 | 2.438 [95% CI 0.602-9.878] p = 0.212 | 2.588 [95% CI 0.592-11.325] p = 0.207 | 3.183 [95% CI 0.776-13.051] p = 0.108 |
|  | RBP4 |  | — | 4.673 [95% CI 1.331-16.404] p = 0.016 | — | 5.120 [95% CI 1.081-24.238] p = 0.040 | 9.423 [95% CI 2.450-36.249] p = 0.001 |
|  | GFAP |  | — | — | 0.034 [95% CI 0.003-0.332] p = 0.004 | 0.029 [95% CI 0.003-0.305] p = 0.003 |  |
| IDI statistics | IDI events |  |  | 0.0487 | 0.0953 | 0.130 | 0.118 |
|  | IDI non-events |  |  | 0.0423 | 0.1171 | 0.146 | 0.125 |

TABLE 5-continued

Multivariate logistic regression with an adjusted clinical model by age, sex and NIHSS.
Model Ischemic Stroke

|  |  | Adjusted Clinical model | Adjusted Clinical model + RBP4 | Adjusted Clinical model + GFAP | Adjusted Clinical model + RBP4 + GFAP | Adjusted Clinical model + RBP4/ GFAP |
|---|---|---|---|---|---|---|
|  | IDI |  | 0.091 (0.0168-0.1652) | 0.2124 (0.0896-0.3351) | 0.276 (0.149-0.403) | 0.243 (0.130-0.356) |
|  | p-value |  | 0.0163 | 0.0006 | $1.98*10^{-5}$ | $2.62*10^{-5}$ |
| Categorical NRI | NRI events | — | 0 | −0.0263 | −0.0263 | 0.5263 |
|  | NRI non-events | — | 0 | 0.32 | 0.44 | 0.08 |
|  | NRI | — | 0 | 0.2937 [0.1039-0.4835] | 0.4137 [0.2126-0.6148] | 0.6063 [0.3354-0.8772] |
|  | p-value | — | — | 0.00242 | **6*10−5** | **1*10−5** |
| ROC curve | AUC | 0.731 (0.605-0.858) | 0.775 (0.648-0.903) | 0.823 (0.712-0.935) | 0.867 (0.763-0.972) | 0.855 (0.747-0.964) |
|  | p-value | ref | 0.4469 | 0.0730 | 0.0400 | 0.0600 |

Looking for cut-off points with maximal specificity for ischemic and/or hemorrhagic stroke the inventors found that a cut-off point of RPB4=57.8 μg/mL and GFAP=0.07 ng/mL for Ischemic stroke lead to a Sensitivity=36.8%, Specificity=100%, PPV=100% and NPV=51% and for Hemorrhagic stroke: Sensitivity=36%, Specificity=100%, PPV=100% and NPV=70%.

Additionally, a cut-off point of RPB4=61 μg/mL and GFAP=0.07 ng/mL for Ischemic stroke lead to a Sensitivity=34.2%, Specificity=100%, PPV=100% and NPV=50% and for Hemorrhagic stroke: Sensitivity=44%, Specificity=100%, PPV=100% and NPV=73%.

Example 2

Selection of Protein Candidate Biomarkers from HPA

Proteins that showed a high expression in brain (cerebral cortex, lateral ventricles, hippocampus and cerebellum) and were low or undetected in other tissues are shown in table 6. Table 7 the list of proteins that appeared to be specific of glial cells, showing an expression profile similar to GFAP (specific of glial cells). Proteins C1orf96, OMG, NRGN, CAC1A, β-synuclein, CARNS1, ADRB1 and Juxtanodin were selected to be analyzed by ELISA immunoassay in serum/plasma samples of stroke patients, based on their SCORE, their function, current literature or availability of commercial immunoassay.

TABLE 6

Top 10 proteins that showed a high expression in brain tissue and low or undetermined in other tissues. The score was calculated by adding 1 for each tissue in which the corresponding protein was low or undetected. The higher the score, the more brain specific protein.

| Name | Abbreviation | ENSEMBL | UniProt | Brain level expresion | SCORE |
|---|---|---|---|---|---|
| Centriole, cilia and spindle-associated protein | C1orf96 | ENSG00000154429 | Q6IQ19 | High | 47 |
| Oligodendrocyte-myelin glycoprotein | OMG | ENSG00000126861 | P23515 | High | 47 |
| Microtubule-associated proteins 1A/1B light chain 3A | MLP3A | ENSG00000101460 | Q9H492 | High | 47 |
| Beta-synuclein | β-synuclein | ENSG00000074317 | Q16143 | High | 47 |
| A-kinase anchor protein 5 | AKAP5 | ENSG00000179841 | P24588 | High | 46 |
| Neurogranin | NRGN | ENSG00000154146 | Q92686 | High | 46 |
| Homer protein homolog 1 | HOME1 | ENSG00000152413 | Q86YM7 | High | 46 |
| Glutamate receptor 2 | GRIA2 | ENSG00000120251 | P42262 | High | 46 |
| Dynamin-1 | DYN1 | ENSG00000106976 | Q05193 | High | 46 |
| Metallothionein-3 | MT3 | ENSG00000087250 | P25713 | High | 46 |

TABLE 7

Top 10 proteins that showed a high expression level in glial cells and were undetected in other cell types. The SCORE was calculated by adding 1 for each cell type in which the corresponding protein was undetected. The higher the score, the more specific glial protein.

| Name | Abbreviation | ENSEMBL | UniProt | Expression level in glia | SCORE |
|---|---|---|---|---|---|
| Carnosine synthase 1 | CARNS1 | ENSG00000172508 | A5YM72 | High | 41 |
| Beta-1 adrenergic receptor | ADRB1 | ENSG00000043591 | P08588 | High | 40 |
| Voltage-dependent P/Q-type calcium channel subunit alpha-1A | CAC1A | ENSG00000141837 | O00555 | High | 40 |
| A-kinase anchor protein 5 | AKAP5 | ENSG00000179841 | P24588 | High | 40 |
| Potassium voltage-gated channel subfamily KQT member 2 | KCNQ2 | ENSG00000075043 | O43526 | High | 39 |
| Oligodendrocyte-myelin glycoprotein | OMG | ENSG00000126861 | P23515 | High | 39 |
| Metallothionein-3 | MT3 | ENSG00000087250 | P25713 | High | 38 |
| Tripartite motif-containing protein 2 | TRIM2 | ENSG00000109654 | Q9C040 | High | 38 |
| Neuromodulin | NEUM | ENSG00000172020 | P17677 | High | 36 |
| Coronin-1A | COR1A | ENSG00000102879 | P31146 | High | 35 |

Analysis of Neurofilaments

Figure 7:
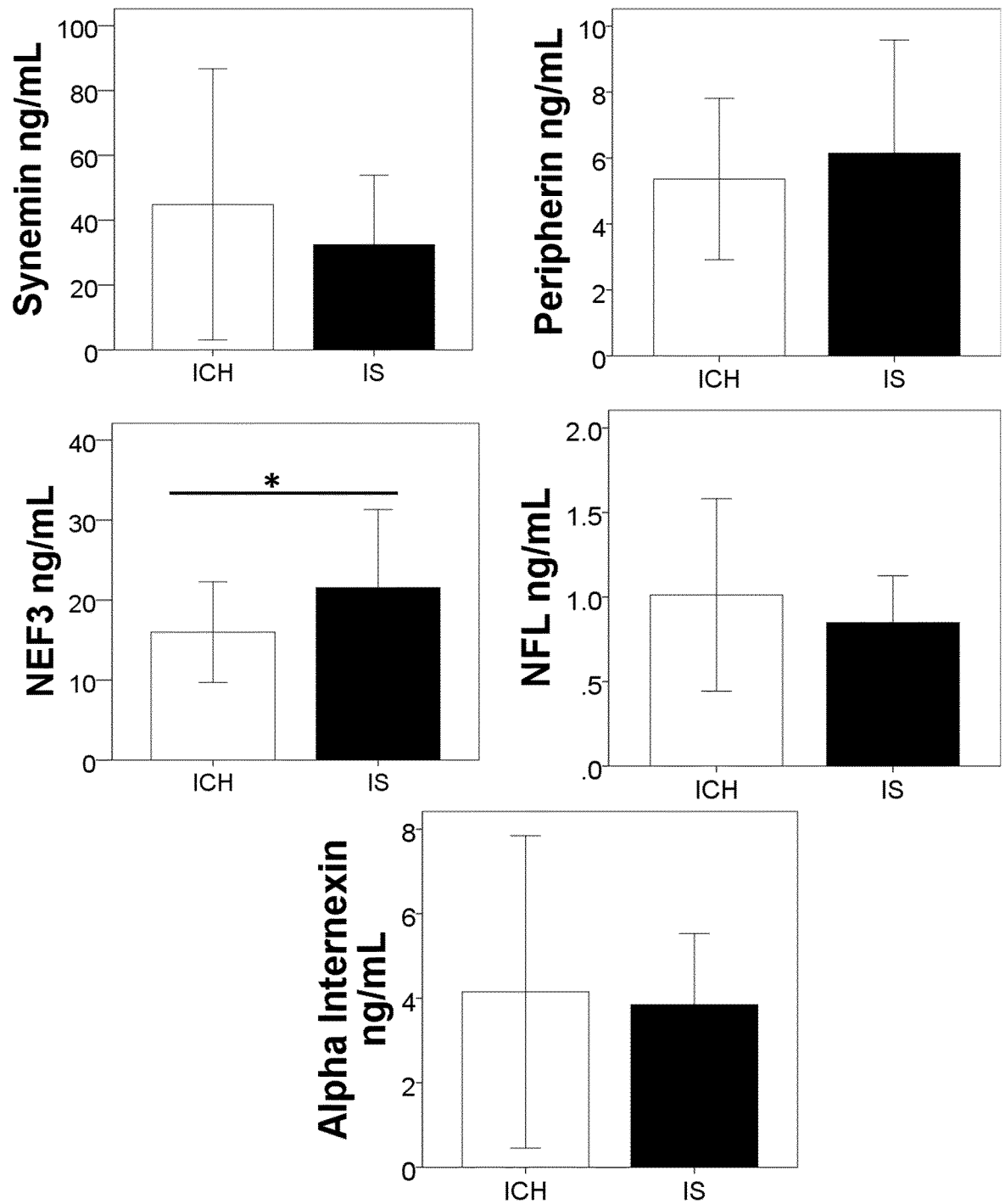
FIG. 7: Circulating levels of Syn, Per, NEF3, NFL and Ina. Only NEF3 showed significant differences between patients that suffered an ICH (n=16) compared to IS (n=15). Mean and standard deviation are represented. * indicates $p<0.05$.

Among the proteins form the family of the neurofilaments only NEF3 showed significant differences between IS and ICH patients (p=0.024) (FIG. 7) and was selected to be analyzed in the whole cohort of 74 stroke patients together with the protein biomarkers selected using data from HPA. Levels of NFH were undetectable in all the analyzed patients.

Levels of Selected Biomarkers in Different Stroke Subtypes

Proteins C1orf96, OMG, NRGN, β-synuclein, CARNS1, CAC1A, ADRB1 selected from HPA-based approach, together with NEF3 from the neurofilament family were analyzed by ELISA immunoassay in serum/plasma samples of 74 stroke patients. Proteins GFAP and RBP4 were also analyzed in this new cohort. This cohort of 74 patients presented NIHSS>4 and had less than 4.5 hours of evolution from symptoms onset. Moreover, IS and ICH patients were balanced by age, gender and etiology. Table 8 shows the main demographic characteristics of the patients that were included in this cohort.

TABLE 8

Main demographic data of the 74 stroke patients that were included in the new cohort. Mean and SD are indicated for continuous variables.

|  | Frequency N (%) |
|---|---|
| Gender (female) | 34 (45.9%) |
| Hypertension | 57 (77%) |
| Dyslipidemia | 36 (48.6%) |
| Diabetes mellitus | 21 (28.4%) |
| Tobbaco | 10 (13.5%) |
| Alcohol | 5 (6.8%) |
| Ischemic stroke | 40 (54.1%) |
| Age (years) | 73.47 ± 11.5 |
| NIHSS (baseline) | 13.2 ± 6.06 |

Figure 8:
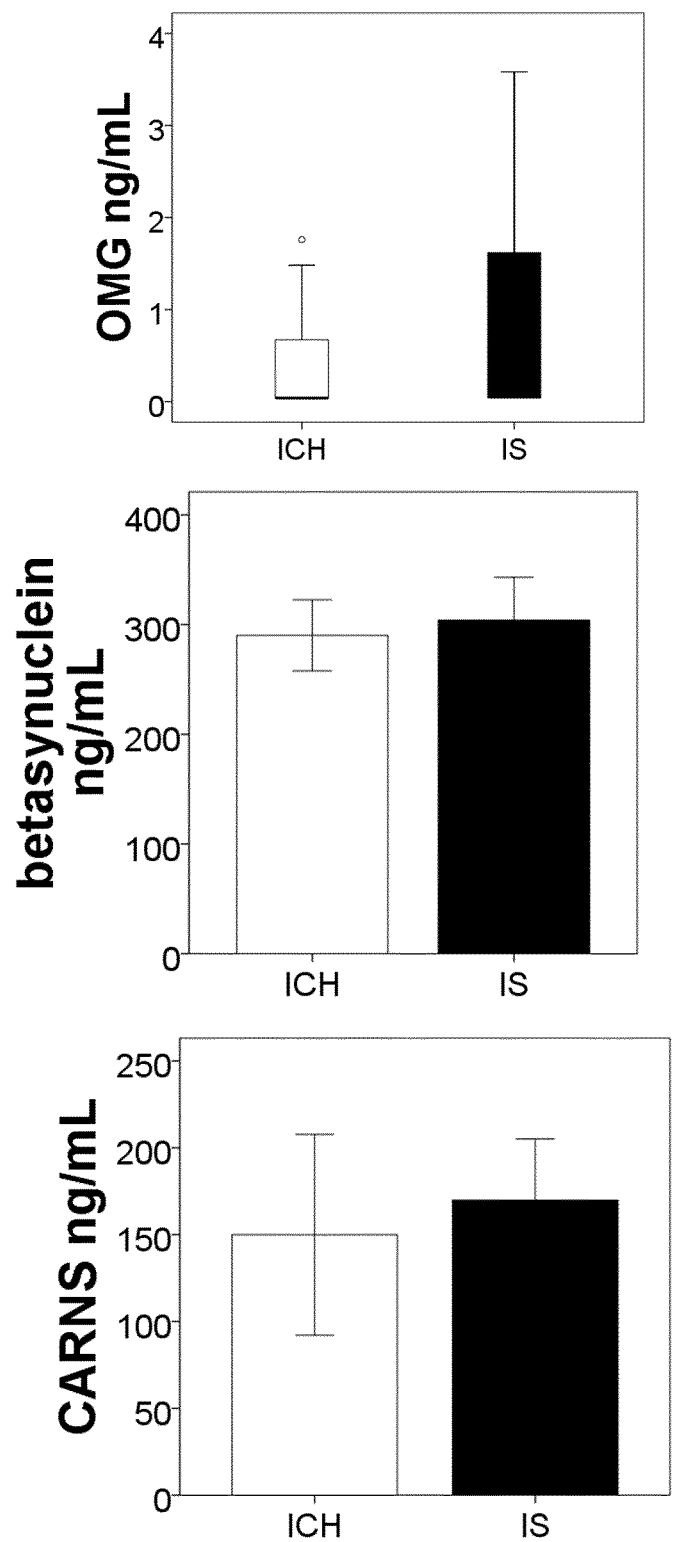
FIG. 8: Levels of proteins OMG, NRGN, ADRB1, β-synuclein, C1orf96, NEF3, CARNS1, CAC1A, JN and GFAP analyzed in the cohort of 40 IS and 34 ICH patients. Box plot represent median and interquartile range. Bar graphs represent mean and SD. * $p<0.05$ ** $p<0.001$.
Figure 8:
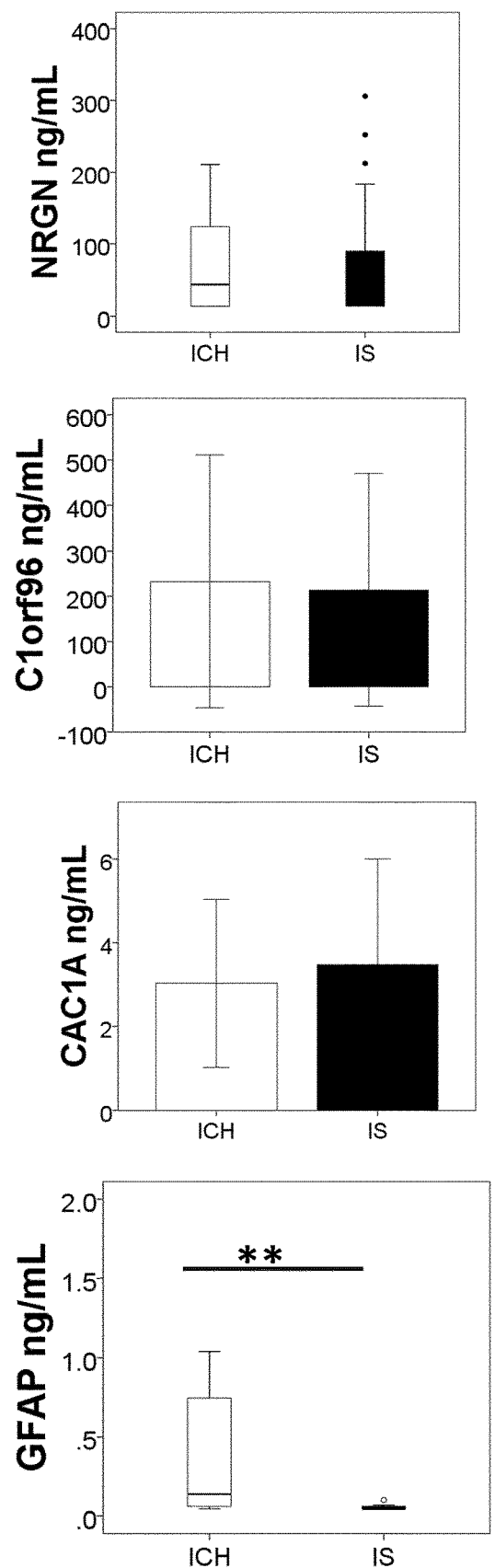
Figure 8:
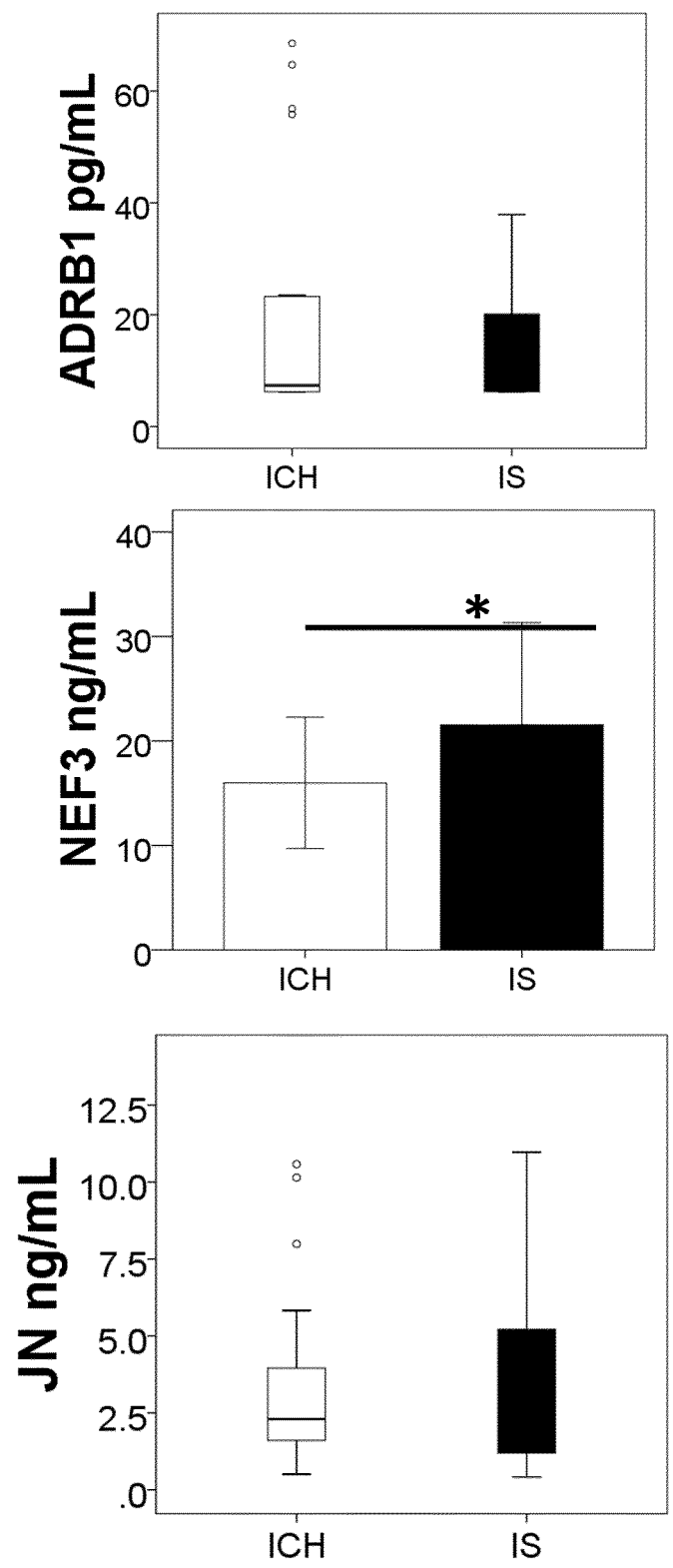

The inventors found significant differences regarding levels of GFAP (p<0.001) and NEF3 (p=0.024) between IS and ICH patients. IS patients also had a trend to have higher levels in β-synuclein (0.136) (FIG. 8). Table 9 shows the levels of each analyzed protein.

TABLE 9

Levels of protein biomarkers analyzed in plasma/serum of IS and ICH patients. Normally distributed variables are indicated as mean ± standard deviation (SD), whereas non-normally distributed show median and interquartile range (IQR).

| Biomarker | Stroke subtype | Mean/median | SD/IQR | p |
|---|---|---|---|---|
| OMG | ICH | 0.039 | (0.039-0.67) | 0.372 |
|  | IS | 0.064 | (0.039-1.62) |  |
| NRGN | ICH | 44.1 | (14.04-124) | 0.655 |
|  | IS | 49.33 | (14.04-89.94) |  |
| ADRB1 | ICH | 7.37 | (6.25-23.29) | 0.456 |
|  | IS | 7.22 | (6.25-19.68) |  |
| β-synuclein | ICH | 290 | ±32.45 | 0.136 |
|  | IS | 304.05 | ±39.15 |  |
| C1orf96 | ICH | 232.32 | ±279.06 | 0.779 |
|  | IS | 213.57 | ±256.78 |  |
| NEF3 | ICH | 15.99 | ±6.29 | 0.024 |
|  | IS | 21.54 | ±9.79 |  |
| CARNS1 | ICH | 149.91 | ±57.81 | 0.168 |
|  | IS | 168.16 | ±35.76 |  |
| CAC1A | ICH | 3.04 | ±2 | 0.453 |
|  | IS | 3.48 | ±2.53 |  |
| JN | ICH | 2.3 | (1.6-3.96) | 0.706 |
|  | IS | 2.4 | (1.21-4.88) |  |
| GFAP | ICH | 0.062 | (0.14-0.75) | <0.001 |
|  | IS | 0.045 | (0.045-0.045) |  |

After univariate analysis the inventors found significant differences regarding alcohol consumption, and found increased systolic and diastolic blood pressure in ICH compared to IS patients (p<0.05) (Table 10)

TABLE 10

Univariate analysis among IS and ICH patients. Normally distributed variables show mean ± SD, whereas non-normally distributed show median and interquartile range.

|  | ICH (n = 34) | IS (n = 40) | P-value |
|---|---|---|---|
| Gender (female) | N = 14 (41.2%) | N = 22 (52.6%) | 0.331 |
| HYPERTENSION | N = 8 (47.8%) | N = 30 (54.5%) | 0.589 |
| DIABETES | N = 30 (57.7%) | N = 8 (40%) | 0.178 |

TABLE 10-continued

Univariate analysis among IS and ICH patients. Normally distributed variables show mean ± SD, whereas non-normally distributed show median and interquartile range.

|  | ICH (n = 34) | IS (n = 40) | P-value |
|---|---|---|---|
| DYSLIPEMIA | N = 19 (51.4%) | N = 19 (54.3%) | 0.803 |
| ATRIAL FIBRILATION | N = 27 (48.2%) | N = 11 (68.8%) | 0.147 |
| CORONOPATHY | N = 32 (50.8%) | N = 6 (66.7%) | 0.372 |
| TOBACCO | N = 35 (56.5%) | N = 3 (30%) | 0.175 |
| ALCOHOL | N = 38 (56.7%) | N = 0 (0%) | 0.02 |
| PREVIOUS STROKE | N = 32 (53.3%) | N = 6 (50%) | 0.833 |
| AGE | 70.56 ± 10.09 | 75.66 ± 12.42 | 0.062 |
| Systolic blood pressure (SBP) | 176.48 ± 34.16 | 160.15 ± 28 | 0.041 |
| Diastolic blood pressure (DBF) | 94 (81-100) | 82.5 (77-90) | 0.015 |
| GLUCEMIA | 126.5 (108-203) | 130 (107-147) | 0.515 |
| NIHSS AT BASELINE | 11.5 (10-19) | 11.5 (8-17) | 0.278 |

Sensitivity and Specificity

Figure 9:
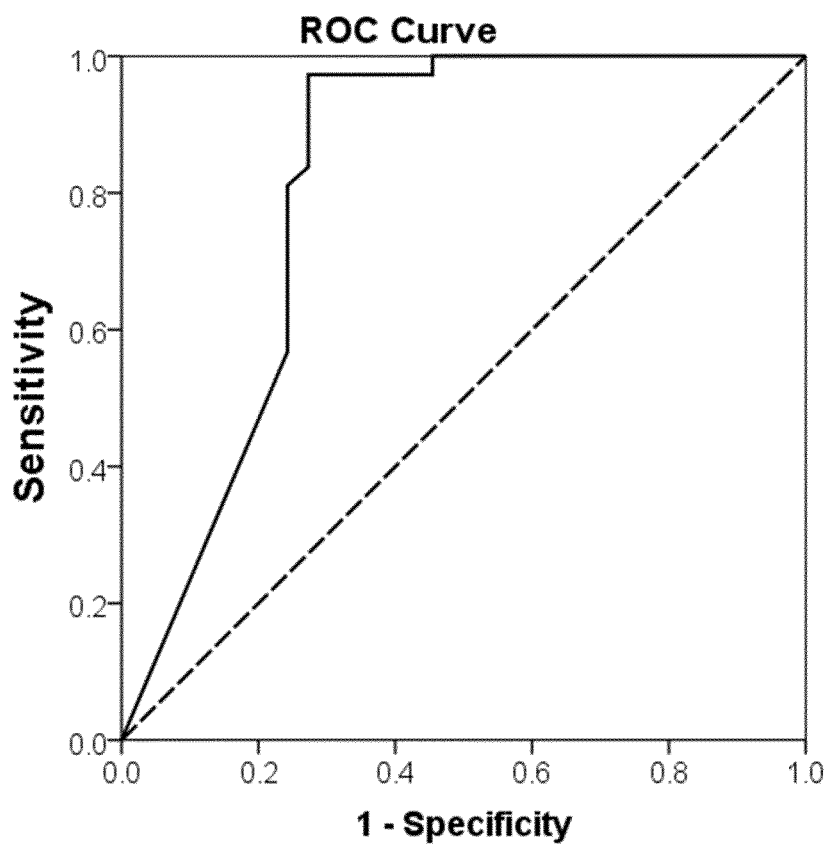
FIG. 9: ROC curves from GFAP (A), NEF3 (B) and β-synuclein (C).
Figure 9:
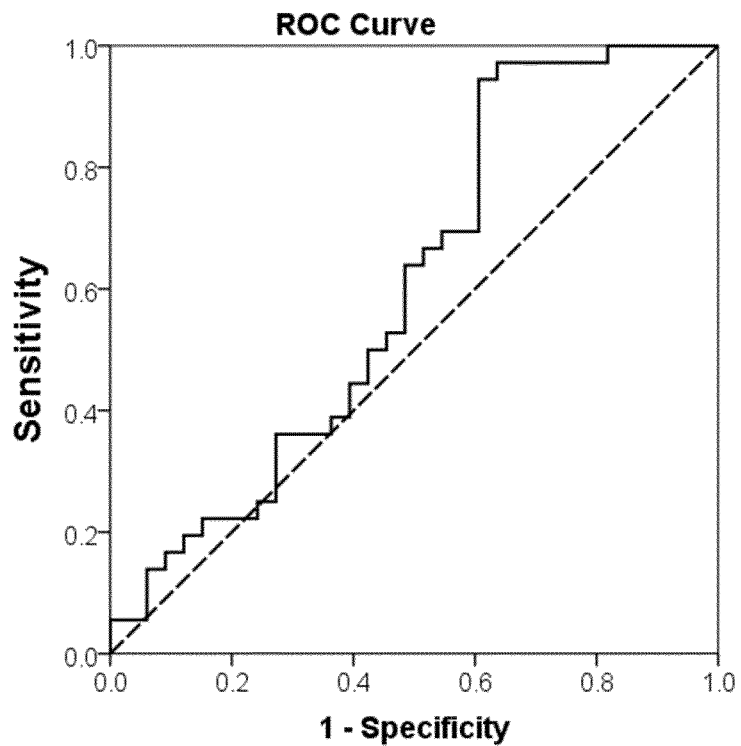
Figure 9:
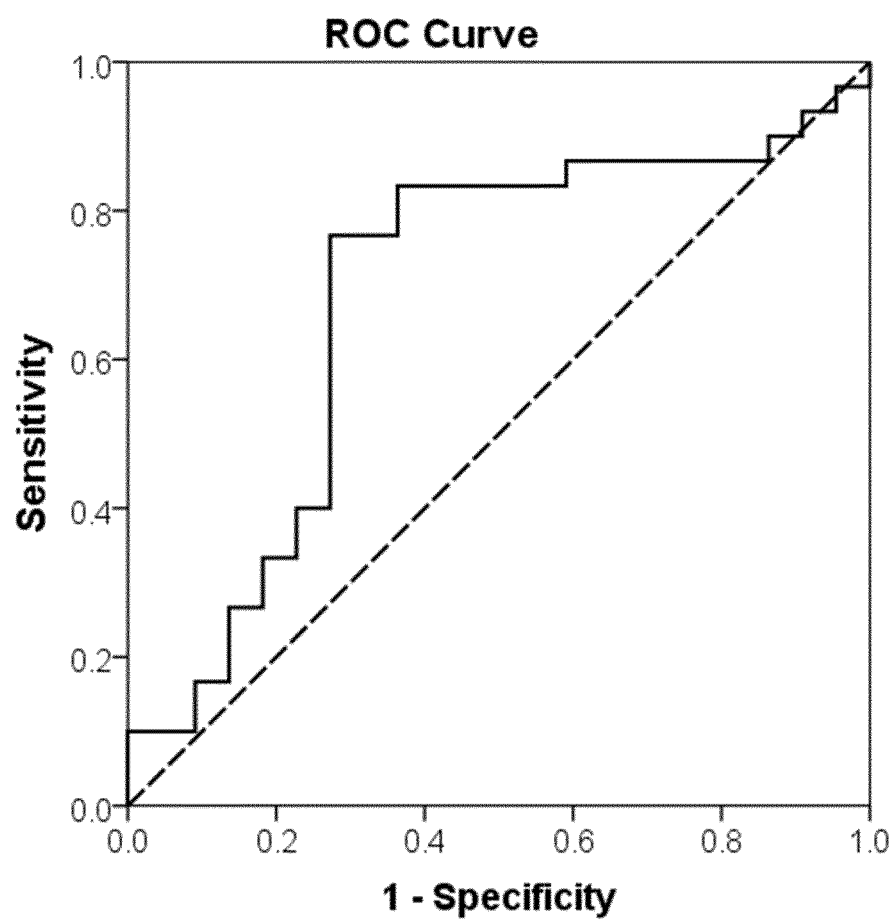
Figure 10:
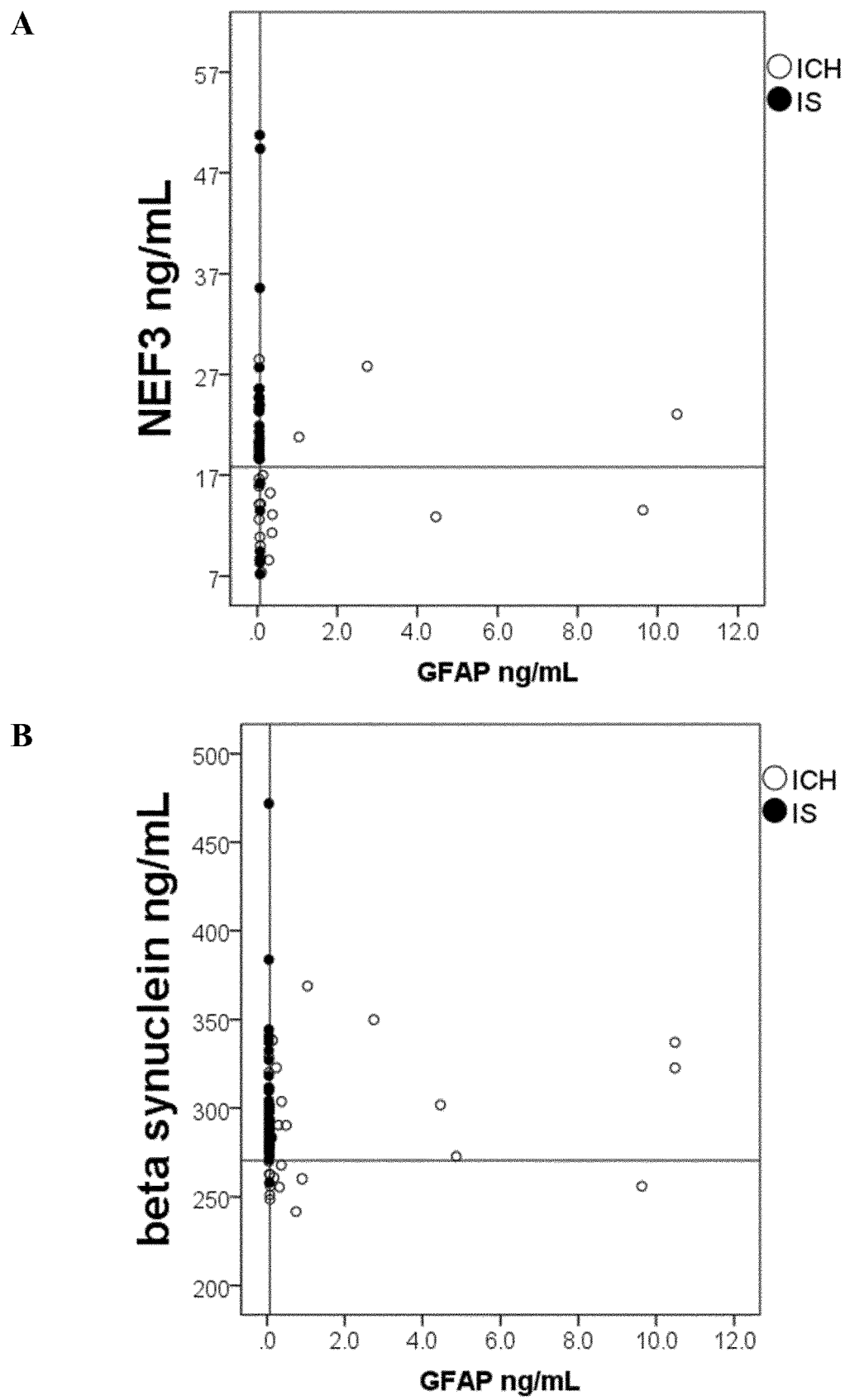
FIG. 10: Dot plot showing the distribution of IS (black circle) and ICH (white circle) patients regarding their levels of A) GFAP and NEF3 or B) GFAP and Beta synuclein. C) shows the % of detection of IS and ICH when GFAP<0.07 is combined with NEF3>17.796 and D) shows the % of detection of IS and ICH when GFAP<0.07 is combined with β-synuclein>270.312.
Figure 10:
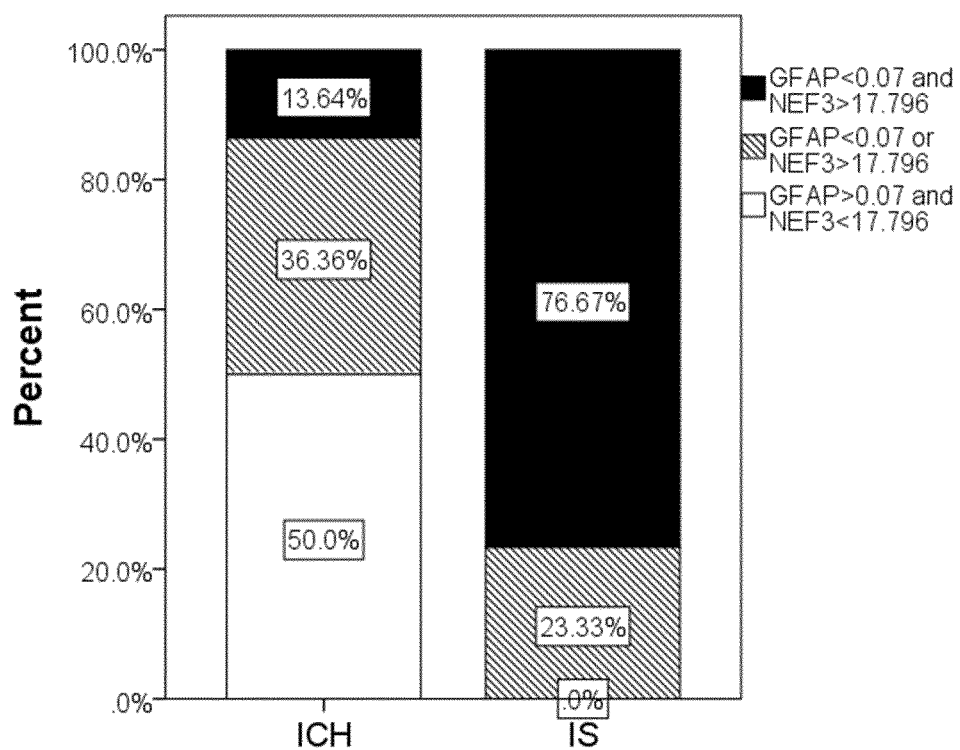
Figure 10:
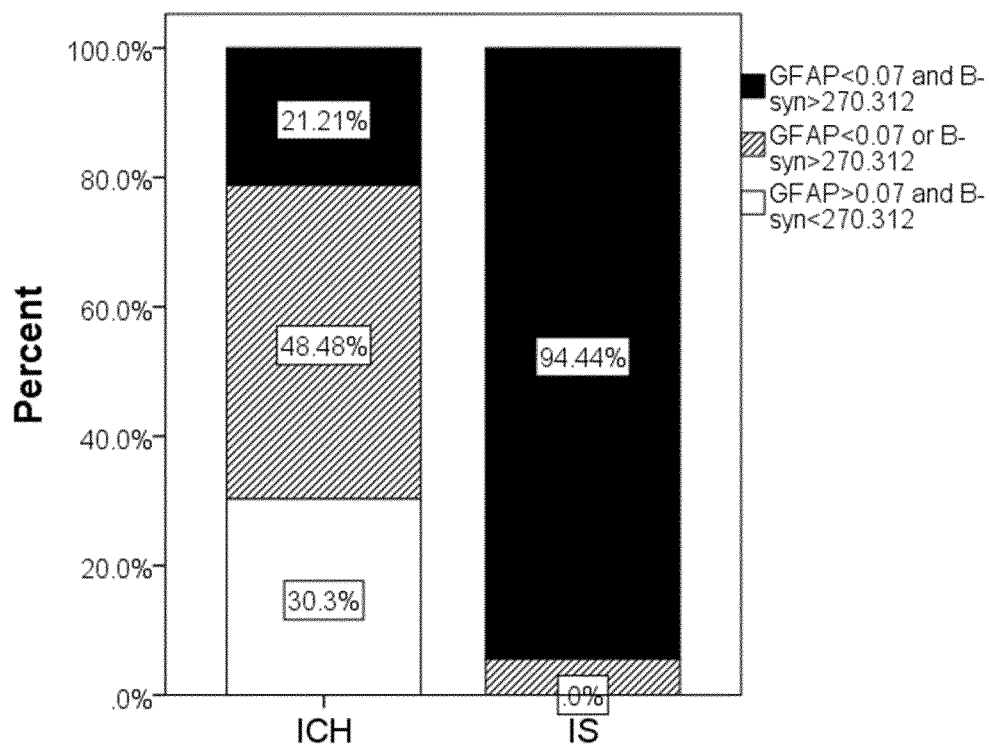

The inventors identified the cut-off points that provided the best sensitivity and specificity by means of ROC curve. Levels of β-synuclein>270.312 ng/mL showed a sensitivity=97.2%, specificity=36.4%, positive predictive value=62.5% (48.55%-75.08%) and negative predictive value=92.31% (63.97%-99.81%). NEF3>17.796 ng/mL showed a sensitivity=76.7%, specificity=72.7%, positive predictive value=79.31% (60.28%-92.01%) and negative predictive value=69.57% (47.08%, 86.79%). Finally, GFAP<0.07 retrieved a sensitivity=97.3%, specificity=72.73%, positive predictive value=80% (65.4%-90.42%), negative predictive value=96% (79.65%-99.9%) (FIG. 9). FIGS. 10A and 10B shows the selection of patients when NEF3>17.796 ng/mL and β-synuclein>270.312 ng/mL were considered together in combination with GFAP. When the inventors combined the biomarkers dicothomized by their corresponding cut-off point, the combination of GFAP<0.07 and NEF3>17.796 ng/mL detected IS subtype with a sensitivity=76.67%, specificity=86.36%, positive predictive value=88.46% (69.85%-97.55%), negative predictive value=73.08% (52.21%-88.43%). On the other hand, the combination of GFAP<0.07 and β-synuclein>270.312 detected IS with a sensitivity=94.44%, specificity=78.79%, positive predictive value=82.93% (67.94%-82.85%), negative predictive value=92.86% (76.5%-99.12%) (FIG. 10C)

Predictive Models

Biomarkers NEF3 and β-synuclein (dichotomized by their corresponding cut-off point) were added into the predictive model composed by GFAP and adjusted by age, gender and NIHSS at baseline and showed an $OR_{adj}$=5.652 (95% CI 0.746-42.803); p=0.094 and $OR_{adj}$=22.487 (0.999-506.38); p=0.05, respectively (Table 11). When GFAP was combined with NEF3 and β-synuclein separately, the combination appeared to be independent predictor of ischemic stroke (16.773 (4.06-69.28); p<0.001, for GFAP/NEF3; and 104.08 (9.82-1103.11); p<0.001 for GFAP/β-synuclein). Neither NEF3 nor β-synuclein increased significantly the accuracy of the predictive model when added to GFAP (based on AUC values), however NEF3 significantly increased the discrimination between subjects who suffered an IS and those with ICH (IDI index 9.72% (3.67, 15.76); p=0.002). In addition, NEF3 significantly reclassified into higher risk categories when added to GFAP or in combination with GFAP (NRI 45.76% (24.374-66.77), p<0.001; and NRI 30% (5.54, 54.46), p=0.016). In order to analyze the performance of the biomarkers NEF3 and β-synuclein together with GFAP in a simple clinical model, the same analysis was performed considering age as the only clinical variable (Table 12). The combination of NEF3 with GFAP as well as β-synuclein with GFAP were independent predictors of IS (16.71 (4.03-69.24); p<0.001 and 48.75 (8.53-278.72); p<0.001). The goodness of fit of all the analyzed models was good (p>0.05). Considering the probabilities that retrieved each predictive model, the prediction of stroke subtype was calculated based on a specificity of 80% (Table 13). When NEF3 was added into the model that contained age, gender, NIHSS and GFAP, 100% of patients that were predicted to be ICH were real ICH, and 94.9% of predicted IS resulted clinically diagnosed IS.

TABLE 11

Comparison between predictive models. ORadj (95% CI) and p-value are given for all logistic regression models. Biomarkers were added to clinical logistic regression model using cut-off points: NEF3 > 17.796 ng/mL, β-synuclein > 270.312 ng/mL and GFAP < 0.07 ng/mL. AUC: Area Under the ROC Curve; area with 95% CI given for each model. Clinical model with GFAP was always used as reference model to compare. Statistically significant are highlighted in bold.
Model Ischemic Stroke

|  |  | Basic clinics | Basic clinics + GFAP | Basic clinics + GFAP + NEF3 | Basic clinics + GFAP + Bsyn | Basic clinics + GFAP/ NEF3 | Basic clinics + GFAP/ Bsyn |
|---|---|---|---|---|---|---|---|
| Logistic regression (OR adj) | Sex | 1.832 (0.661-5.078); p = 0.245 | 3.854 (0.678-21.917); p = 00128 | 7.726 (0.506-117.956); p = 0.142 | 7.42 (0.79-69.581); p = 0.079 | 1.5 (0.27-8.49); p = 0.65 | 8.09 (0.88-74.19); p = 0.065 |
|  | Age | 1.045 (0.99-1.093); p = 0.054 | 1.061 (1.001-1.125); p = 0.045 | 1.086 (1.003-1.17); p = 0.041 | 1.056 (0.994-1.122); p = 0.076 | 1.06 (0.99-1.1); p = 0.089 | 1.05 (0.99-1.12); p = 0.097 |
|  | NIHSS | 0.927 (0.851-1.011); p = 0.085 | 1.024 (0.884-1.185); p = 0.754 | 1.136 (0.893-1.445); p = 0.298 | 1.011 (0.87-1.176); p = 0.882 | 0.974 (0.85-1.1); p = 0.70 | 0.99 (0.86-1.1); p = 0.859 |
|  | GFAP | — | 220.086 (15.862-3053.791); p < 0.0001 | $1.602*10^{11}$ (—) | 218.569 (11.884-4019.9); p < 0.0001 | — | — |

TABLE 11-continued

Comparison between predictive models. ORadj (95% CI) and p-value are given for all logistic regression models. Biomarkers were added to clinical logistic regression model using cut-off points: NEF3 > 17.796 ng/mL, β-synuclein > 270.312 ng/mL and GFAP < 0.07 ng/mL. AUC: Area Under the ROC Curve; area with 95% CI given for each model. Clinical model with GFAP was always used as reference model to compare. Statistically significant are highlighted in bold.

Model Ischemic Stroke

|  |  | Basic clinics | Basic clinics + GFAP | Basic clinics + GFAP + NEF3 | Basic clinics + GFAP + Bsyn | Basic clinics + GFAP/NEF3 | Basic clinics + GFAP/Bsyn |
|---|---|---|---|---|---|---|---|
|  | NEF3 | — | — | 5.652 (0.746-42.803); p = 0.094 | — | — | — |
|  | BetaSyn | — | — | — | 22.487 (0.999-506.38); p = 0.05 | — | — |
| Combination |  |  |  |  |  | 16.773 (4.06-69.28); p < 0.001 | 104.08 (9.82-1103.11); p < 0.001 |
| IDI statistics | IDI events | — | — | 2.55% | 1.49% | -3.64% | 0.83% |
|  | IDI non-events | — | — | 7.17% | 1.91% | -1.28% | 1.19% |
|  | IDI | — | — | 9.72% (3.67, 15.76) | 3.4% (-1.9, 8.69) | -4.92% (-17.91, 8.07) | 2.03% (-5.53, 9.58) |
|  | p-value | — | ref | p = 0.002 | p = 0.209 | p = 0.458 | p = 0.599 |
| Categorical NRI 90% | NRI events | — | — | 36.67% | 8.33% | 30% | 8.33% |
|  | NRI non-events | — | — | 9.09% | 0% | 0% | -9.09% |
|  | NRI | — | — | 45.76% (24.74, 66.77) | 8.33% (-6.59, 23.25) | 30% (5.54, 54.46) | -0.76 (-20.2, 18.69) |
|  | p-value | — | ref | p < 0.001 | p = 0.274 | p = 0.016 | p = 0.939 |
| ROC curve | AUC | — | 0.936 (0.869-1) | 0.95 (0.893-1) | 0.95 (0.903-0.998) | 0.918 (0.847-0.989) | 0.947 (0.897-0.997) |
|  | p-value | — | ref | 0.621 | 0.252 | 0.565 | 0.409 |

TABLE 12

Comparison between predictive models. ORadj (95% CI) and p-value are given for all logistic regression models. Biomarkers were added to clinical logistic regression model using cut-off points: NEF3 > 17.796 ng/mL, β-synuclein > 270.312 ng/mL and GFAP < 0.07 ng/mL. AUC: Area Under the ROC Curve; area with 95% CI given for each model. Clinical model with GFAP was always used as reference model to compare. Statistically significant are highlighted in bold.

|  |  | Age + GFAP | Age + GFAP + NEF3 | Age + GFAP + Bsyn | Age + GFAP/NEF3 | Age + GFAP/Bsyn |
|---|---|---|---|---|---|---|
| Logistic regression (OR adj) | Age | 1.06 (1-1.13); p = 0.03 | 1.08 (1-1.16); p = 0.029 | 1.06 (1-1.13); p = 0.044 | 1.06 (0.995-1.13); p = 0.072 | 1.06 (0.998-1.12); p = 0.059 |
|  | GFAP | 124.91 (13.69-1139.6); p < 0.001 | 8*10^7 (0-inf), p = 0.998 | 100.24 (10.37-968.35), p < 0.001 | — | — |
|  | NEF3 | — | 5.43 (0.86-34.4), p = 0.072 |  | — | — |
|  | Bsyn | — |  | 9.08 (0.72-114.83); p = 0.088 | — | — |
|  | Combination | — | — | — | 16.71 (4.03-69.24); p < 0.001 | 48.75 (8.53-278.72); p < 0.001 |
| IDI stastitics | IDI events | — | 1.15% | 1.67% | 0.68% | 1.06% |
|  | IDI non-events | — | 5.98% | 0.995% | -2.74% | 0.44% |
|  | IDI | — | 7.13% (1.23, 13.03) | 2.67% (-1.9, 7.23) | -2.06 (-15.56, 11.43) | 1.5% (-5.71, 8.71) |
|  | p-value | — | p = 0.018 | p = 0.252 | p = 0.765 | p = 0.683 |
| Categorical NRI | NRI events | — | 10% | 11.11% | 20% | 2.78% |
|  | NRI non-events | — | 0 | -6.06% | -13.64% | -24.24% |

TABLE 12-continued

Comparison between predictive models. ORadj (95% CI) and p-value are given for all logistic regression models. Biomarkers were added to clinical logistic regression model using cut-off points: NEF3 > 17.796 ng/mL, β-synuclein > 270.312 ng/mL and GFAP < 0.07 ng/mL. AUC: Area Under the ROC Curve; area with 95% CI given for each model. Clinical model with GFAP was always used as reference model to compare. Statistically significant are highlighted in bold.

|  |  | Age + GFAP | Age + GFAP + NEF3 | Age + GFAP + Bsyn | Age + GFAP/ NEF3 | Age + GFAP/ Bsyn |
|---|---|---|---|---|---|---|
|  | NRI | — | 10% (−6.91, 26.9) | 5.05% (−8.05, 18.15) | 6.36% (−17.75, 30.47) | −21.46% (−40.76, −2.17) |
|  | p-value | — | p = 0.246 | p = 0.45 | p = 0.605 | p = 0.029 |
| ROC curve | AUC | 0.927 (0.858-0.997) | 0.947 (0.893-1) | 0.947 (0.896-0.997) | 0.917 (0.845-0.988) | 0.935 (0.875-0.995) |
|  | p-value | ref | 0.383 | 0.131 | 0.605 | 0.029 |

TABLE 13

Prediction of stroke subtype based on the probabilities retrieved by the corresponding predictive model. An specificity on 80% was considered as threshold. Clinics included age, gender and NIHSS at baseline. Percentages indicate the proportion of predicted subtype that was correctly classified as ICH or IS.

| Predicted subtype (80% specificity) | Stroke subtype | |
|---|---|---|
|  | ICH | IS |
| Clinics + GFAP | | |
| ICH | 96% | 4% |
| unknown | 43.8% | 56.2% |
| IS | 6.9% | 93.1% |
| Clinics + GFAP + NEF3 | | |
| ICH | 100% | 0% |
| unknown | 50% | 50% |
| IS | 4.1% | 94.9% |
| Clinics + GFAP + β-synuclein | | |
| ICH | 96% | 4% |
| unknown | 66.7% | 33.3% |
| IS | 17.1% | 82.9% |
| Clinics + GFAP/NEF3 | | |
| ICH | 85% | 15% |
| unknown | 60% | 40% |
| IS | 4.3% | 95.6% |
| Clinics + GFAP/β-synuclein | | |
| ICH | 91.7% | 8.3% |
| unknown | 40.6% | 89.4% |
| IS | 5.8% | 94.2% |

Example 3

Sensitivity and Specificity of CARNS1

Figure 11:
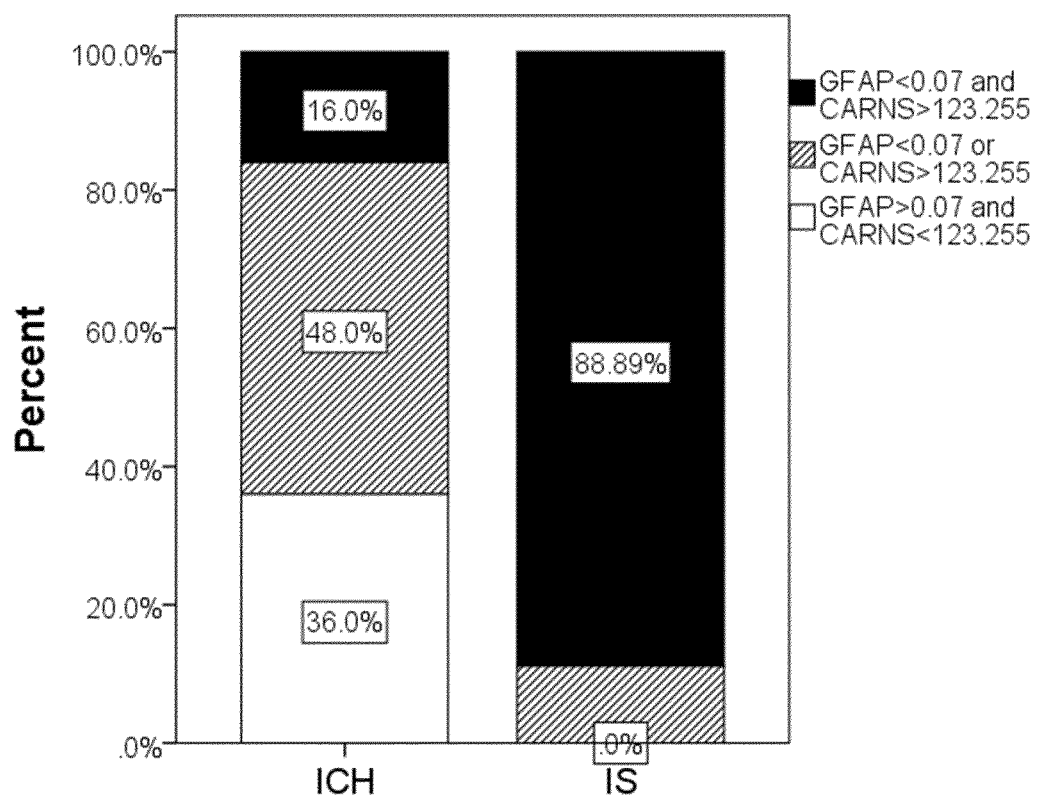
FIG. 11: Stacked bar graphs in which the % of detection of IS and ICH is showed, when GFAP<0.07 combined with CARNS1>123.255 were considered.
Figure 12:
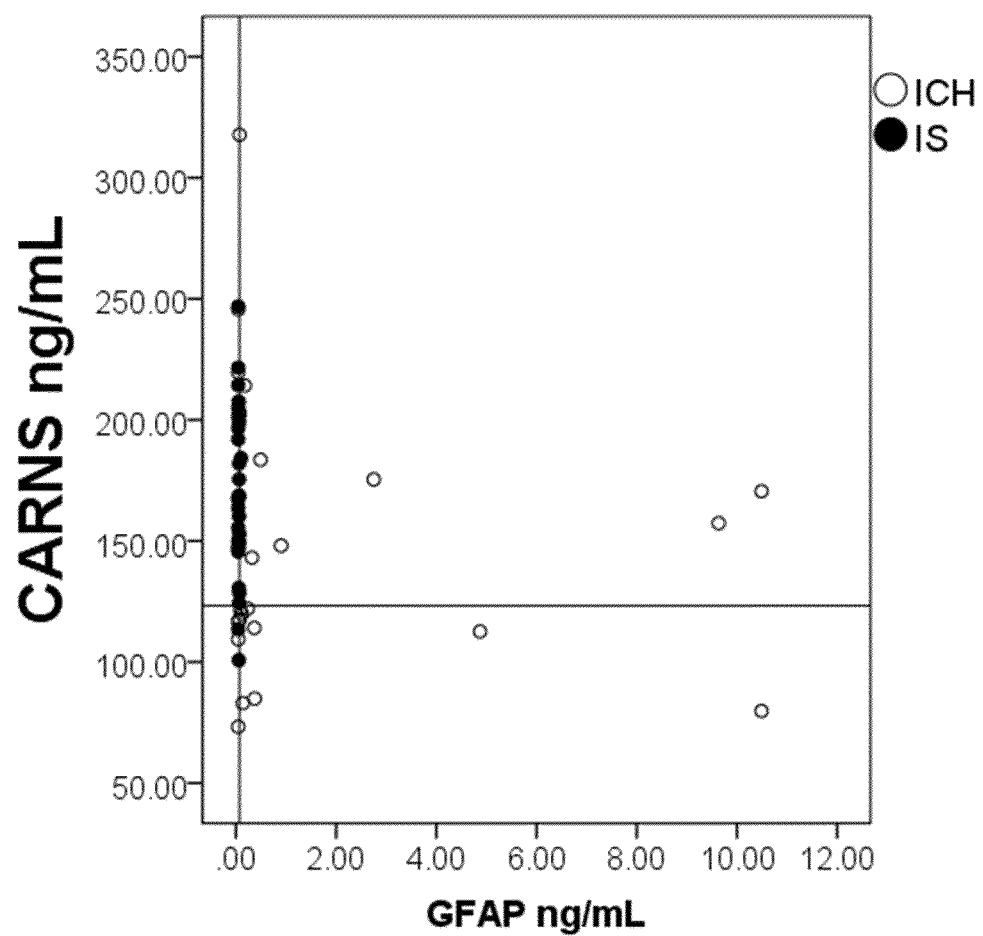
FIG. 12: Dot plots showing the distribution of IS (black circle) and ICH (white circle) patients regarding their levels of GFAP and CARNS1. Cut-off values of GFAP=0.07 and CARNS1=123.255 are highlighted.

Additionally for GFAP, NEF3 and Beta-synuclein, the inventors identified by means of ROC curve the best cut-off point for CARNS1. CARNS1>123.255 ng/mL reported a sensitivity of 92%, a specificity of 48%, positive predictive value=65.79% (48.65%-80.37%) and negative predictive value=85.71% (57.19%-98.22%). When combined with GFAP<0.07, CARNS1>123.255 reported a sensitivity of 89.89% and a specificity of 84% for IS with a PPV=85.71% (67.33%-95.97%) and a NPV of 87.5% (67.64%-97.34%) (FIG. 11)

Predictive Models

The inventors performed a logistic regression including all the clinical variables that reported significant differences among IS and ICH in the univariate analysis. Only SBP (systemic blood pressure) remained as independent predictor of stroke subtype (data not shown). The inventors developed new predictive models for IS stroke including SBP, together with age, gender and NIHSS at baseline as clinical variables, and added consecutively GFAP<0.07, NEF3>17.796 and CARNS1>123.255. When added to the clinical model together with GFAP, NEF3 resulted a predictor of IS with a trend $OR_{adj}$=7.511 (95% CI 0.698-80.868); p=0.096), and CARNS1 showed very similar results $OR_{adj}$=7.565 (95% CI 0.691-82.84); p=0.097). Additionally, NEF3 significantly increased the discrimination between subjects who suffered an IS and those with ICH (IDI index 10.37% (2-18.7); p=0.015). Both NEF3 and CARNS1 reclassified into higher risk categories when added to GFAP (NRI 32.2% (11.8-52.7), p=0.002 and NRI 30.95% (6.04-55.86), p=0.01, respectively)) (Table 14).

TABLE 14

Comparison between predictive models. ORadj (95% CI) and p-value are given for all logistic regression models. Biomarkers were added to clinical logistic regression model using cut-off points: NEF3 >17.796 ng/mL, CARNS1 >123.255 ng/mL and GFAP <0.07 ng/mL. AUC: Area Under the ROC Curve; area with 95% CI given for each model. Clinical model with GFAP was always used as reference model to compare. Statistically significant are highlighted in bold.

Model Ischemic Stroke

|  |  | Clinics | clinics + GFAP | clinics + GFAP + NEF3 | clinics + GFAP + CARNS1 |
|---|---|---|---|---|---|
| Logistic regression (OR adj) | Sex | 1.325 (0.418-4.195); p = 0.632 | 2.178 (0.456-16.029); p = 0.272 | 7.517 (0.33-171.419); p = 0.206 | 4.763 (0.32-70.908); p = 0.257 |
|  | Age | 1.079 (1.018-1.144); p = 0.011 | 1.071 (1.001-1.146); p = 0.046 | 1.085 (0.995-1.184); p = 0.064 | 1.07 (0.963-1.189); p = 0.209 |

TABLE 14-continued

Comparison between predictive models. ORadj (95% CI) and p-value are given for all logistic regression models. Biomarkers were added to clinical logistic regression model using cut-off points: NEF3 >17.796 ng/mL, CARNS1 >123.255 ng/mL and GFAP <0.07 ng/mL. AUC: Area Under the ROC Curve; area with 95% CI given for each model. Clinical model with GFAP was always used as reference model to compare. Statistically significant are highlighted in bold.

Model Ischemic Stroke

|  |  | Clinics | clinics + GFAP | clinics + GFAP + NEF3 | clinics + GFAP + CARNS1 |
|---|---|---|---|---|---|
|  | NIHSS | 0.913 (0.828-1.01); p = 0.066 | 1.007 (0.866-1.171); p = 0.929 | 1.176 (0.89-1.554); p = 0.254 | 0.964 (0.778-1.194); p = 0.736 |
|  | SBP | 0.975 (0.954-0.997); p = 0.024 | 0.986 (0.957-1.016); p = 0.346 | 0.999 (0.961-1.038); p = 0.963 | 0.96 (0.9161.006); p = 0.085 |
|  | GFAP | — | 104.694 (7.975-1374.44); p < 0.001 | $2.25 \times 10^{11}$ (0-inf); p = 0.998 | 77.812 (3.009-2011.92); p = 0.009 |
|  | NEF3 | — |  | 7.511 (0.698-80.868); p = 0.096 |  |
|  | CARNS1 | — |  | — | 7.565 (0.691-82.84); p = 0.097 |
| IDI statistics | IDI events | — |  | 2.34% | 3.07% |
|  | IDI non-events | — |  | 8.02% | 2.33% |
|  | IDI p-value | — | ref | 10.37% (2%, 18.7%) p = 0.015 | 5.4% (−1.32%, 12.11%) p = 0.115 |
| Categorical NRI 90% | NRI events | — |  | 22.2% | 16.67% |
|  | NRI non-events | — |  | 10% | 14.29% |
|  | NRI p-value | — | ref | 32.2% (11.8%, 52.7%) p = 0.002 | 30.95% (6.04%, 55.86%) (p = 0.015) |
| ROC curve | AUC | — | 0.922 (0.832-1) | 0.952 (0.895-1) | 0.952 (0.899-1) |
|  | p-value | — | ref | n.s. | n.s. |

Similarly as previously reported, considering the probabilities that retrieved each predictive model, the prediction of stroke subtype was calculated based on a specificity of 80% (Table 15). When both CARNS1 and NEF3 were added into the model that contained age, gender, NIHSS, SBP and GFAP 100% of patients that were predicted to be ICH were real ICH. The percentage of IS correctly predicted slightly increased when NEF3 was added to the model.

TABLE 15

Prediction of stroke subtype based on the probabilities retrieved by the corresponding predictive model. A specificity of 80% was considered as threshold. Clinics included age, gender and NIHSS at baselineand SBP. Percentages indicate the proportion of predicted subtype that was correctly classified as ICH or IS.

|  | Stroke subtype | |
|---|---|---|
| Predicted subtype (80% specificity) | ICH | IS |
| Clinics (SBP) + GFAP | | |
| ICH | 95.4% | 4.6% |
| unknown | 38.4% | 61.6% |
| IS | 7.7% | 92.3% |

TABLE 15-continued

Prediction of stroke subtype based on the probabilities retrieved by the corresponding predictive model. A specificity of 80% was considered as threshold. Clinics included age, gender and NIHSS at baselineand SBP. Percentages indicate the proportion of predicted subtype that was correctly classified as ICH or IS.

|  | Stroke subtype | |
|---|---|---|
| Predicted subtype (80% specificity) | ICH | IS |
| Clinics (SBP) + GFAP + NEF3 | | |
| ICH | 100% | 0% |
| unknown | 54.5% | 45.5% |
| IS | 0.04% | 99.96% |
| Clinics (SBP) + GFAP + CARNS1 | | |
| ICH | 100% | 0% |
| unknown | 40% | 60% |
| IS | 5.2% | 94.8% |

The sensitivity and specificity data of individual markers and combinations for ischemic stroke are summarized in Table 16.

TABLE 16

Specificity and sensitivity to differentiate IS stroke from ICH using different biomarkers.

| Biomarkers | sensitivity | specificity | positive predictive value | negative predictive value |
|---|---|---|---|---|
| NEF3 >17.796 ng/mL | 76.7% | 72.7% | 79.31% (60.28%-92.01%) | 69.57% (47.08%, 86.79%) |
| β-synuclein >270.312 ng/mL | 97.2% | 36.4% | 62.5% (48.55%-75.08%) | 92.31% (63.97%-99.81%) |
| CARNS1 >123.255 ng/mL | 92% | 48% | 65.79% (48.65%-80.37%) | 85.71% (57.19%-98.22%) |

TABLE 16-continued

Specificity and sensitivity to differentiate IS stroke from ICH using different biomarkers.

| Biomarkers | sensitivity | specificity | positive predictive value | negative predictive value |
|---|---|---|---|---|
| GFAP <0.07 | 97.3% | 72.73% | 80% (65.4%-90.42%) | 96% (79.65%-99.9%) |
| GFAP <0.07 and NEF3 >17.796 ng/mL | 76.67% | 86.36% | 88.46% (69.85%-97.55%) | 73.08% (52.21%-88.43%) |
| GFAP <0.07 and β-synuclein >270.312 | 94.44% | 78.79% | 82.93% (67.94%-82.85%) | 92.86% (76.5%-99.12%) |
| GFAP <0.07, CARNS1 >123.255 | 89.89% | 84% | 85.71% (67.33%-95.97%) | 87.5% (67.64%-97.34%) |
| GFAP + β-synuclein + NEF3 | 75.86% | 81.25% | 88% 68.78%, 97.45%) | 65% (40.78%-84.61%) |
| GFAP + carnosin1 + NEF3 | 65% | 93.33% | 92.86% (66.13%, 99.82%) | 66.67% (43.03%, 85.41%) |
| GFAP + carnosin1 + RBP4 | 77.78% | 88% | 87.5% (67.64%, 97.34%) | 78.57% (59.05%, 91.7%) |
| GFAP + β-synuclein + RBP4 | 80.56% | 90.91% | 90.62% (74.98%, 98.02%) | 81.08% (64.84%, 92.04%) |
| GFAP + NEF3 + RBP4 | 66.67% | 95.45% | 95.24% (76.18%, 99.88%) | 67.74% (48.63%, 83.32%) |

The sensitivity and specificity data of individual markers and combinations for hemorrhagic stroke are summarized in Table 17.

TABLE 17

Specificity and sensitivity to differentiate ICH stroke from IS using different biomarkers.

| Biomarkers | sensitivity | specificity | positive predictive value | negative predictive value |
|---|---|---|---|---|
| NEF3 <17.796 ng/mL | 72.7% | 76.7% | 69.57% (47.08%, 86.79%) | 79.31% (60.28%-92.01%) |
| β-synuclein <270.312 ng/mL | 36.4% | 97.2% | 92.31% (63.97%-99.81%) | 62.5% (48.55%-75.08%) |
| CARNS1 <123.255 ng/mL | 48% | 92% | 85.71% (57.19%-98.22%) | 65.79% (48.65%-80.37%) |
| GFAP >0.07 | 72.73% | 97.3% | 96% (79.65%-99.9%) | 80% (65.4%-90.42%) |
| GFAP >0.07 and NEF3 <17.796 ng/mL | 50% | 100% | 100% (71.51%-100%) | 73% (57.06%-85.78%) |
| GFAP >0.07 and β-synuclein <270.312 | 30.3% | 100% | 100% (69.15%-100%) | 61% (47.44%-73.45%) |
| GFAP >0.07, CARNS1 <123.255 | 36% | 100% | 100% (66.37%-100%) | 56.3% (46.73%-77.02%) |
| GFAP + β-synuclein + NEF3 | 22.7% | 100% | 100% (47.82%-100%) | 63% (47.55%-76.79%) |
| GFAP + carnosin1 + NEF3 | 33.3% | 100% | 100% (47.82%-100%) | 53.7% (47.19% 82.71%) |
| GFAP + carnosin1 + RBP4 | — | — | — | — |
| GFAP + β-synuclein + RBP4 | 3% | 100% | 100% (2.5%-100% | 52.94% (40.45%-65.17%) |
| GFAP + NEF3 + RBP4 | 4.5% | 100% | 100% (2.5%-100%) | 58.8% (44.17%-72.42%) |

The invention claimed is:

1. A method for differentiating ischemic stroke from hemorrhagic stroke in a patient and for treating said patient, or for selecting a patient suffering stroke for a therapy with an antithrombotic agent or with an agent capable of reducing blood pressure and for treating said patient, comprising
   a) determining the level of glial fibrillary acidic protein (GFAP) in a sample of said patient in combination with the level of one or more markers selected from the group consisting of neurofilament medium polypeptide (NEF3), β-synuclein, carnosine synthase 1 (CARNS1) and retinol binding protein 4 (RBP4),
   b) comparing said levels with a corresponding reference value,
   wherein a level of GFAP in said sample lower than the corresponding reference value and a level of NEF3, β-synuclein, CARNS1 and/or RBP4 higher than the corresponding reference value is indicative that the patient suffers ischemic stroke, or is indicative that the patient is a candidate for a therapy with an antithrombotic agent, or
   wherein a level of GFAP in said sample higher than the reference value and a level of NEF3, β-synuclein, CARNS1 and/or RBP4 lower than the corresponding reference value is indicative that the patient suffers hemorrhagic stroke, or is indicative that the patient is a candidate for a therapy with an agent capable of reducing blood pressure, and
   c) administering an antithrombotic agent to the patient identified to suffer ischemic stroke or identified to be a candidate for a therapy with an antithrombotic agent, or administering an agent capable of reducing blood pressure to the patient identified to suffer hemorrhagic stroke or identified to be a candidate for a therapy with an agent capable of reducing blood pressure.

2. The method according to claim 1 wherein the antithrombotic agent is a thrombolytic agent.

3. The method according to claim 2 wherein the thrombolytic agent is a plasminogen activator.

4. The method according to claim 3 wherein the plasminogen activator is tissue plasminogen activator.

5. The method according to claim 1 wherein the reference value for GFAP is 0.07 ng/ml, the reference value for NEF3 is 17.796 ng/ml, the reference value for β-synuclein is 270.312 ng/ml, the reference value for CARNS1 is 123.255 ng/ml and/or the reference value for RBP4 is 49.53 µg/ml.

6. The method according to claim 1 wherein the sample is a biofluid.

7. The method according to claim 6 wherein the biofluid is plasma or serum.

8. The method according to claim 1 further comprising determining one or more clinical parameters.

9. The method according to claim 8 wherein the clinical parameter is hypertension and wherein hypertension in the patient is indicative that the patient suffers ischemic stroke or that the patient is a candidate for a therapy with a thrombolytic agent.

10. The method according to claim 1 wherein step a) comprises determining the level of GFAP in a sample of said patient in combination with the level of NEF3 or CARNS1.

11. A method for differentiating ischemic stroke from hemorrhagic stroke in a patient and for treating said patient, or for selecting a patient suffering stroke for a therapy with an antithrombotic agent or with an agent capable of reducing blood pressure and for treating said patient, comprising
   a) determining the level of RBP4 in a sample of said patient and
   b) comparing said level with a reference value,
   wherein a level of RBP4 in said sample higher than the reference value is indicative that the patient suffers ischemic stroke or that the patient is a candidate for a therapy with an antithrombotic agent or
   wherein a level of RBP4 in said sample lower than the reference value is indicative that the patient suffers hemorrhagic stroke or that the patient is a candidate for a therapy with an agent capable of reducing blood pressure, and
   c) administering an antithrombotic agent to the patient identified to suffer ischemic stroke or identified to be a candidate for a therapy with an antithrombotic agent, or administering an agent capable of reducing blood pressure to the patient identified to suffer hemorrhagic stroke or identified to be a candidate for a therapy with an agent capable of reducing blood pressure.

12. The method according to claim 11 wherein the antithrombotic agent is a thrombolytic agent.

13. The method according to claim 12 wherein the thrombolytic agent is a plasminogen activator.

14. The method according to claim 13 wherein the plasminogen activator is tissue plasminogen activator.

15. The method according to claim 11 wherein the reference value for RBP4 is 49.53 µg/ml.

16. The method according to claim 11 wherein the sample is a biofluid.

17. The method according to claim 16 wherein the biofluid is plasma or serum.

18. The method according to claim 11 further comprising determining one or more clinical parameters.

19. The method according to claim 18 wherein the clinical parameter is hypertension and wherein hypertension in the patient is indicative that the patient is a candidate for a therapy with a thrombolytic agent that the patient is a candidate for a therapy with an agent capable of reducing blood pressure.

20. The method according to claim 11 wherein the levels of the RBP4 protein are determined within the first hours after stroke.

21. The method according to claim 20 wherein the levels of the RBP4 protein are determined less than 24 hours after symptom onset.

22. The method according to claim 21 wherein the levels of the RBP4 protein are determined less than 6 hours after symptom onset.

23. The method according to claim 22 wherein the levels of the RBP4 protein are determined within the first 4.5 hours from symptom onset.

* * * * *

UNITED STATES PATENT AND TRADEMARK OFFICE
CERTIFICATE OF CORRECTION

PATENT NO. : 10,520,513 B2
APPLICATION NO. : 15/533095
DATED : December 31, 2019
INVENTOR(S) : Joan Montaner Vilallonga et al.

It is certified that error appears in the above-identified patent and that said Letters Patent is hereby corrected as shown below:

On the Title Page

Item (72), Inventor "Joan Montaner Viallonga" should read -Joan Montaner Vilallonga- Item (30), the Foreign Application Priority Data "14382492" should read -14382492.8-

Signed and Sealed this
Seventeenth Day of March, 2020

Andrei Iancu
*Director of the United States Patent and Trademark Office*

UNITED STATES PATENT AND TRADEMARK OFFICE
CERTIFICATE OF CORRECTION

PATENT NO. : 10,520,513 B2  
APPLICATION NO. : 15/533095  
DATED : December 31, 2019  
INVENTOR(S) : Joan Montaner Villalonga et al.

It is certified that error appears in the above-identified patent and that said Letters Patent is hereby corrected as shown below:

On the Title Page

Item (12), "Montaner Viallonga , et al." should read -Montaner Villalonga, et al.-

Item (72), Inventor "Joan Montaner Viallonga" should read -Joan Montaner Villalonga- Item (30), the Foreign Application Priority Data "14382492" should read -14382492.8-

This certificate supersedes the Certificate of Correction issued March 17, 2020.

Signed and Sealed this  
Twenty-fifth Day of August, 2020

Andrei Iancu  
*Director of the United States Patent and Trademark Office*